(12) United States Patent
Thomas

(10) Patent No.: US 7,147,649 B2
(45) Date of Patent: Dec. 12, 2006

(54) TEMPORARY VASCULAR FILTERS

(75) Inventor: John Thomas, Chapel Hill, NC (US)

(73) Assignee: Duke University, Durham, NC (US)

( * ) Notice: Subject to any disclaimer, the term of this patent is extended or adjusted under 35 U.S.C. 154(b) by 725 days.

(21) Appl. No.: 10/343,028

(22) PCT Filed: Jul. 30, 2001

(86) PCT No.: PCT/US01/23868

§ 371 (c)(1),
(2), (4) Date: Jan. 27, 2003

(87) PCT Pub. No.: WO02/11812

PCT Pub. Date: Feb. 14, 2002

(65) Prior Publication Data

US 2003/0208227 A1    Nov. 6, 2003

Related U.S. Application Data

(60) Provisional application No. 60/223,190, filed on Aug. 4, 2000.

(51) Int. Cl.
*A61M 29/00* (2006.01)
(52) U.S. Cl. ...................... 606/200; 606/194
(58) Field of Classification Search ............... 606/200, 606/194, 198, 191
See application file for complete search history.

(56) References Cited

U.S. PATENT DOCUMENTS 6,273,901 B1 *  8/2001  Whitcher et al. ........... 606/200
6,342,063 B1 *  1/2002  DeVries et al. ............ 606/200
2002/0045916 A1  4/2002  Gray et al.

FOREIGN PATENT DOCUMENTS

| WO | WO 99/22673 | 5/1999 |
|---|---|---|
| WO | WO 01/54617 | 8/2001 |

* cited by examiner

*Primary Examiner*—Vy Q. Bui
(74) *Attorney, Agent, or Firm*—Nixon & Vanderhye P.C.

(57) ABSTRACT

Blood filters (10a, 10b) sized and configured to be positioned within a vascular vessel include a plurality of anchoring arms (22) having a removable sleeve (22-2) for temporarily anchoring the blood filter to a vessel wall. In especially preferred embodiments, the removable sleeve (22-2) is formed of bioabsorbable material. When the filter (10a, 10b) is deployed, it is this removable sleeve (22-2) which comes into contact with the inner tissue wall of the patient's blood vessel (typically the inferior vena cava). When it is desired to remove the filter, endothelization of the sleeve (22-2) has typically occurred but since the sleeves are a removable (separable) component part of the anchoring arms (22), the entire filter device (10a, 10b) can be retrieved thereby leaving the endothelized sleeves (22-2) remaining in place on the interior wall of the patient's vascular vesse. However, such sleeves (22-2) will be absorbed over time (preferably by means of hydrolysis) since they are formed of a bioabsorbable polymeric material. In such a manner, the filters (10a, 10b) of the present invention allow relatively easy retrieval while minimizing (if not preventing entirely) harm to the vascular endothelium.

19 Claims, 26 Drawing Sheets

TEMPORARY VASCULAR FILTERS

This application is the US national phase of international application PCT/US01/23868 filed 30 Jul. 2001 which designated the U.S.

CROSS-REFERENCE TO RELATED APPLICATION

This application is based on, and claims domestic priority benefits under 35 USC §119(e) from, U.S. Provisional Application Ser. No. 60/223,190 filed on Aug. 4, 2000, the entire content of which is expressly incorporated hereinto by reference.

FIELD OF THE INVENTION

The present invention relates generally to the field of vascular filters, especially thrombus blood clot filters, and methods. More specifically, the present invention relates to temporary (removable) emobolus blood clot filters and methods especially useful for placement in a patient's inferior vena cava (IVC).

BACKGROUND AND SUMMARY OF THE INVENTION

Temporary immobilization and a number of medical procedures subject the patient to the risk of pulmonary embolism. This risk can be significantly reduced by the use of a filter implant. Currently available filter devices are not easily or safely removable after they have remained in place for more than approximately two weeks. The use of a permanent filter device would not be desirable when temporary protection against pulmonary embolism is needed, especially in younger patients. A temporary filter device that can be easily and safely removed after the threat of pulmonary embolism is over is most desirable.

Temporary blood clot filters are well known as evidenced from the following non-exhaustive list of prior publications and U.S. Patents (the entire content of each being expressly incorporated hereinto by reference): Hagspiel et al, "Inferior vena cava filters: An update", Applied Radiology, pp. 20–34 (November 1998); U.S. Pat. No. 6,007,558; U.S. Pat. No. 5,984,947; U.S. Pat. No. 5,976,172; U.S. Pat. No. 5,893,869; U.S. Pat. No. 5,836,968; U.S. Pat. No. 5,853,420; U.S. Pat. No. 5,836,969; U.S. Pat. No. 5,928,261; U.S. Pat. No. 6,051,015; U.S. Pat. No. 5,746,767; U.S. Pat. No. 5,634,942; U.S. Pat. No. 5,626,605; U.S. Pat. No. 5,601,595; U.S. Pat. No. 5,415,630 and U.S. Pat. No. 5,383,887.

While a variety of proposals for removable blood clot filters exist in the art, improvements are still desired. For example, it would especially be desirable if a temporary blood filter could be implanted in a patient's inferior vena cava and remain therein for a reasonable time, yet be capable of withdrawal without causing damage to the vessel wall. It is towards fulfilling such a need that the present invention is directed.

Broadly, therefore, the present invention relates to a blood filter which is sized and configured to be positioned within a vascular vessel comprising a plurality of anchoring arms for temporarily anchoring the blood filter to a wall of the vascular vessel. Importantly, the anchoring arms include a removable sleeve. In especially preferred embodiments, the removable sleeve is formed of a bioabsorbable material. Thus, when the filter of the present invention is deployed, it is this removable sleeve which comes into contact with the inner tissue wall of the patient's blood vessel (typically the inferior vena cava). When it is desired to remove the filter, endothelization of the sleeve has typically occurred but since the sleeves are a removable (separable) component part of the anchoring arms, the entire filter device can be retrieved thereby leaving the endothelized sleeves remaining in place on the interior wall of the patient's blood vessel. However, such sleeves will be absorbed over time (preferably by means of hydrolysis) since they are formed of a bioabsorbable polymeric material. In such a manner, the filters 10 of the present invention allow relatively easy retrieval while minimizing (if not preventing entirely) harm to the vascular endothelium.

These and other aspects and advantages will become more apparent after careful consideration is given to the following detailed description of the preferred exemplary embodiments thereof.

BRIEF DESCRIPTION OF THE ACCOMPANYING DRAWINGS

Reference will hereinafter be made to the accompanying drawings, wherein like reference numerals throughout the various FIGURES denote like structural elements, and wherein;

FIG. 5A is an elevational view of a delivery system that may be employed in accordance with the present invention, while

DETAILED DESCRIPTION OF THE INVENTION

Figure 1A:
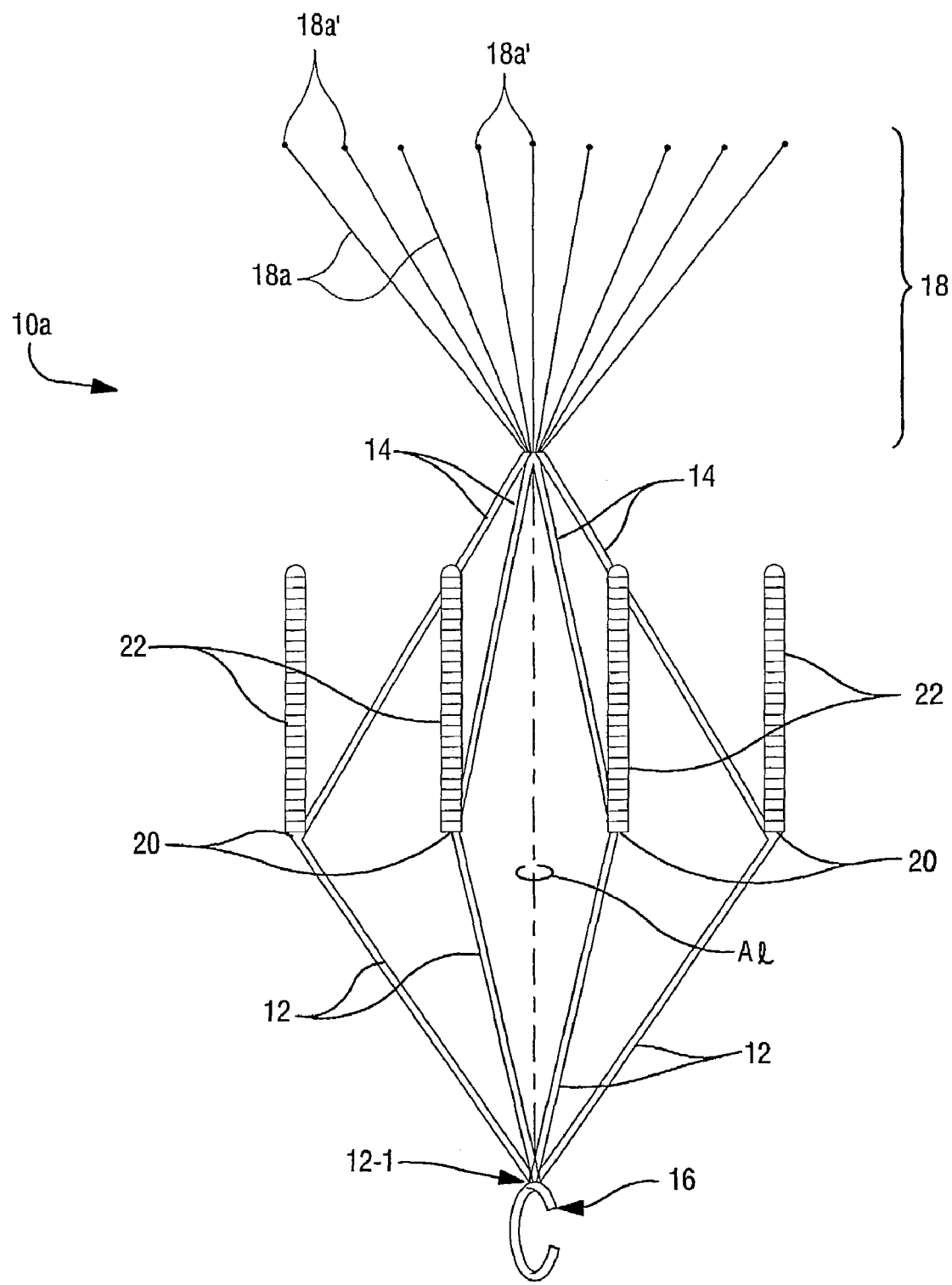
FIGS. 1A and 1B are perspective views which depict particularly preferred embodiments of vascular filters in accordance with the present invention.
Figure 1B:
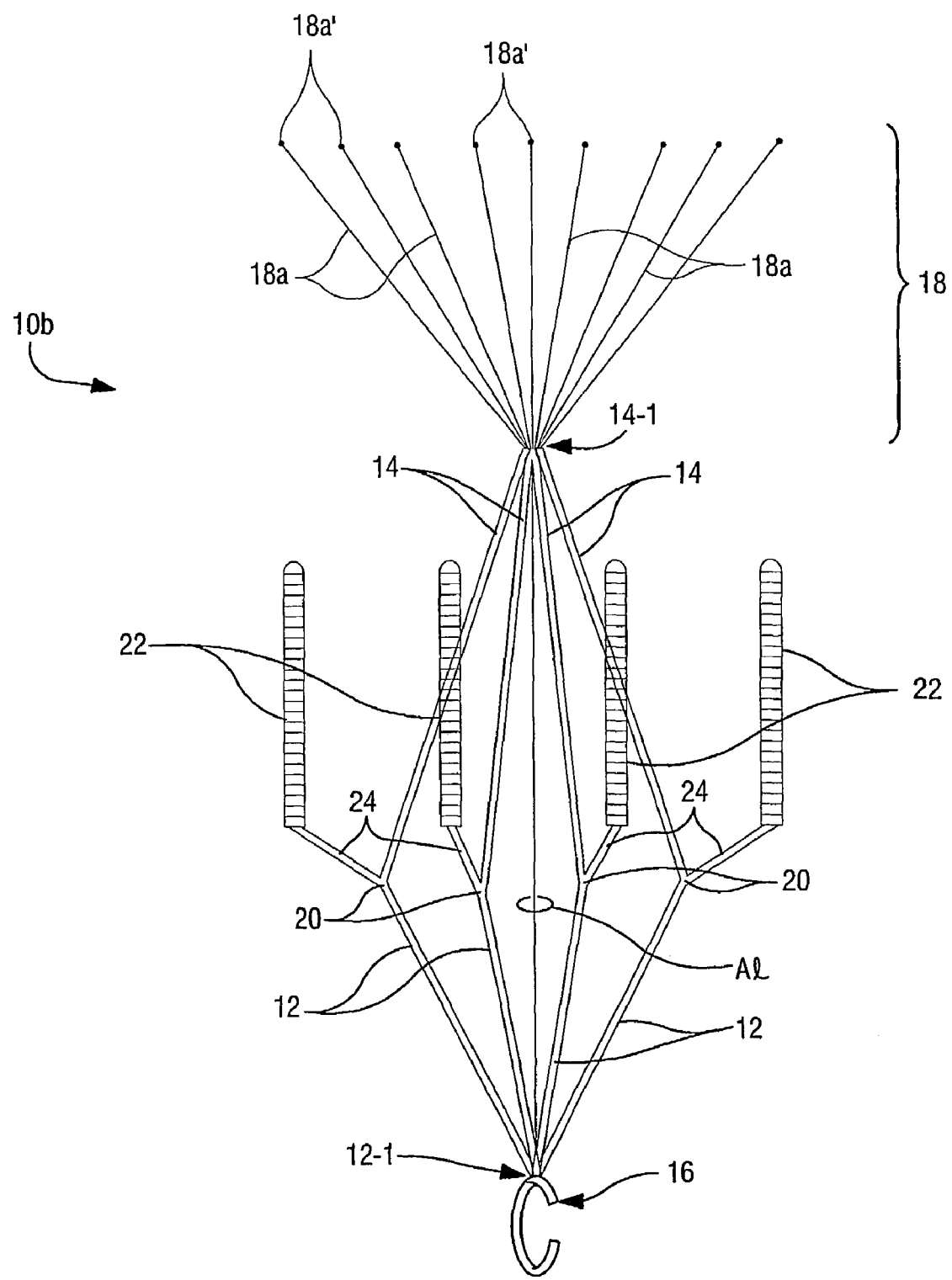

Preferred vascular filters 10a, 10b in accordance with the present invention are shown in accompanying FIGS. 1A and 1B, respectively, as including paired proximal and distal support arm portions 12, 14 which, in the expanded configuration shown in FIGS. 1A and 1B, radiate divergently from the elongate axis $A_l$ of the filters 10a, 10b. The angle between these proximal and distal support arm portions 12, 14 is most preferably about 135°+/− when the filter 10a, 10b is in its expanded configuration. As will be discussed in greater detail below, a hook 16 is provided at the proximal juncture 12-1 of the proximal support arm portions 12, 14.

The blood filter devices 10 of this invention are provided with a distal blood-filtering portion 18. More specifically, the distal juncture 14-1 of the distal support arm portions 14 is most preferably attached to the proximal end of a plurality of filter arms (a few if which are identified by reference numeral 18a in FIGS. 1A and 1B). These filter arms 18a thus radiate divergently away from the longitudinal axis $A_l$ of the filters 10a, 10b, in the distal direction (that is, assume a generally conical configuration) and serve to trap or filter embolus blood clots from the patient's blood stream.

Importantly, the support arm portions 12, 13 are provided at their respective intermediate junctures 20 with a respective anchoring arm 22 so that the plurality of anchoring arms 22 are circumferentially spaced-apart from one another about the longitudinal axis $A_l$ of the filters 10a, 10b. Specifically, as shown in FIGS. 1A and 1B, the anchoring arms 22 extend from the intermediate junctures of the proximal and distal support arm portions 12, 14, in a generally distal direction substantially parallel to the elongate axis $A_l$ of the filters 10a, 10b. As shown in the embodiment of the filter 10a of FIG. 1A, these anchoring arms 22 extend directly from the intermediate junctures 20 of the support arms 12, 14, whereas in the embodiment of FIG. 1B, these anchoring arms 22 are provided with an extension arm section 24. The extension arm section 24 may be provided so as to facilitate easier removal of the filter 10b and minimize (if not prevent entirely) endothelization of the support arm portions 12 and/14.

Figure 2A:
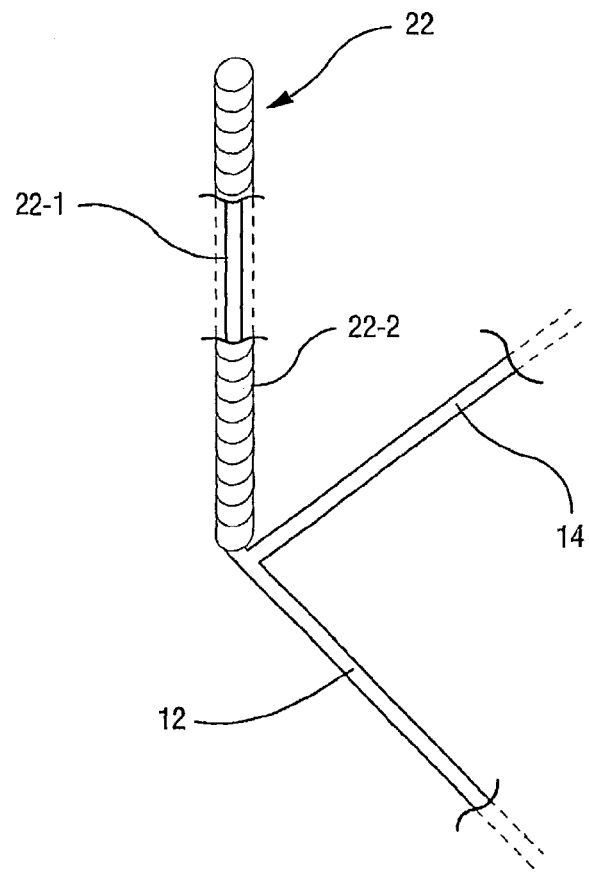
FIGS. 2A and 2B are enlarged perspective views of the anchoring arms that are employed in the vascular filters of FIGS. 1A and 1B, respectively.
Figure 2B:
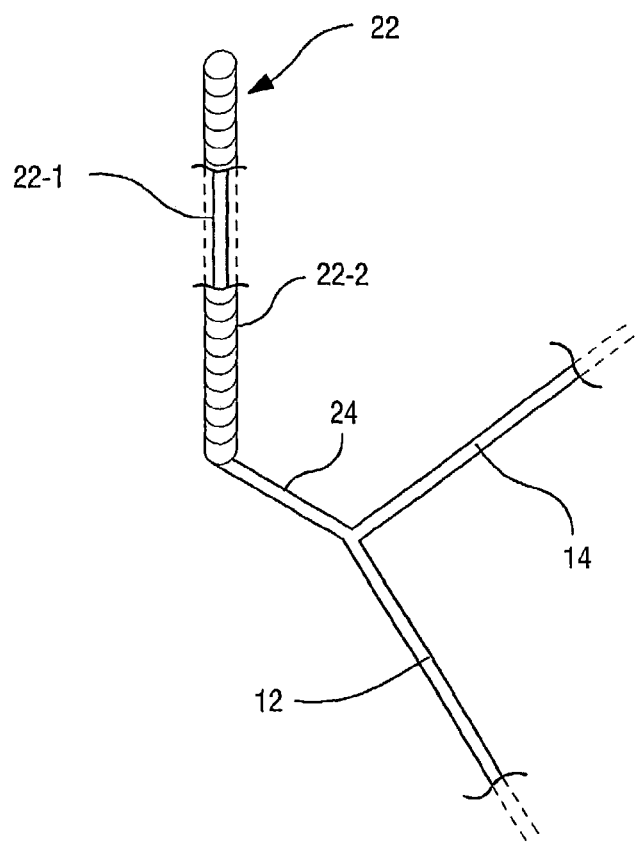

As is perhaps shown in FIGS. 2A and 2B, the anchoring arms 22 are most preferably formed by an inner anchoring arm 22-1 having a substantial longitudinal portion thereof covered by a removable sleeve 222. Since the removable sleeve 22-2 will remain in the patient's vascular tissue following retrieval of the device, it is important that the sleeve 22-2 be formed of a biologically compatible (biocompatible) material, such as for example, biocompatible metals such as stainless steel, titanium and nickel alloys (e.g., NITINOL® alloys), or biocompatible polymeric materials such as silicones, polyolefins, cellulose esters, biologically absorbable polymers and the like.

Advantageously, the sleeves 22-2 are formed for a biologically absorbable (bioabsorbable) material, most preferably a hydrolyzable surgical suture material. As shown in FIGS. 2A and 2B, the sleeve 22-2 may be formed by wrapping a bioabsorbable surgical suture monofilament around the periphery of the inner anchoring arm 22-1. The sleeve 22-2 may thus be removed as a unit from the inner anchoring arm 22-1, the purpose and function of which will be described in greater detail below.

Virtually any bioabsorbable polymeric material may be employed in the practice of the present invention to provide the removable sleeve 22-2. In this regard, the sleeve 22-2 may be formed of copolymers of glycolide with lactide or ε-caprolactone comonomers may satisfactorily be employed. Such bioabsorbable copolymers are commercially available from the ETHICON division of Johnson & Johnson, Inc., Somerville, N.J., under the registered trademarks VICRYL® (a synthetic monofilament absorbable sterile suture material comprised of a copolymer of 90% glycolide and 10% L-lactide, coated with polyglactin 370 and calcium stearate) and MONOCRYL® (a monofilament absorbable sterile suture material comprised of a copolymer of glycolide and ε-caprolactone). Other monofilament suture material that may be employed includes bioabsorbable polyesters, such as poly(p-dixanone), commercially available from the ETHICON division of Johnson & Johnson, Inc., Somerville, N.J., under the registered trademark PDS II®.

It is presently preferred that the bioabsorbable polymeric material be in the form of a monofilament which is wrapped around the inner anchoring arm 22-1 as shown in FIGS. 2A and 2B as such an embodiment is believed to be less traumatic on the vascular endothelium. However, if desired and/or if needed for a particular patient situation, the bioabsorbable material may be molded onto the inner anchoring arm as a monolithic removable coating. Furthermore, the inner anchoring arm may itself be structurally configured into a variety of ways. Possible exemplary forms of the anchoring arms are shown in accompanying FIGS. 3A–3F.

Figure 3A:
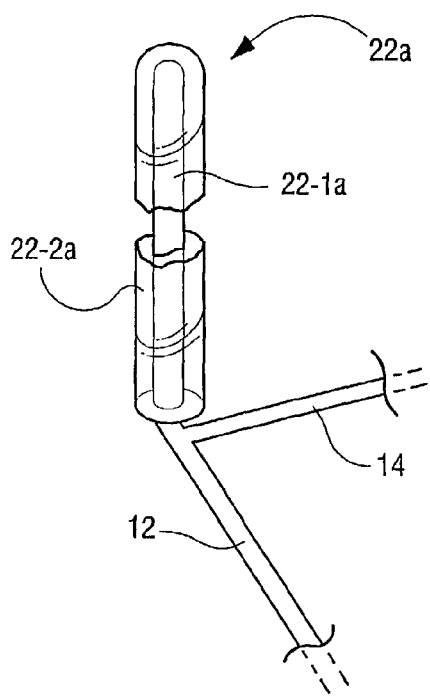
FIGS. 3A–3F are enlarged perspective views which depict various exemplary structural configurations of the anchoring arms that may be employed in the vascular filters of the present invention.

For example, in the embodiment shown in FIG. 3A, the anchoring arm 22a is generally cylindrical in shape and includes a generally cylindrically shaped inner anchoring arm 22-1 a which is coated with a generally cylindrically shaped removable tubular sleeve 22-2a formed of a molded bioabsorbable polymeric material. The external surface of the sleeve 22-2a may be smooth or serrated and the tip may be blunt or pointed as may be desired. In order to ensure removeablilty, a slight (but meaningful) space is provided between the inner anchoring arm 22-1a and the sleeve 22-2a so that these two structural components are in a relatively loose fitting relationship with one another. The shape of the sleeve 22-2a can be modified, however, to facilitate a relatively tight fit within the delivery system at the same time allow adequate contact with the vessel wall.

Figure 3B:
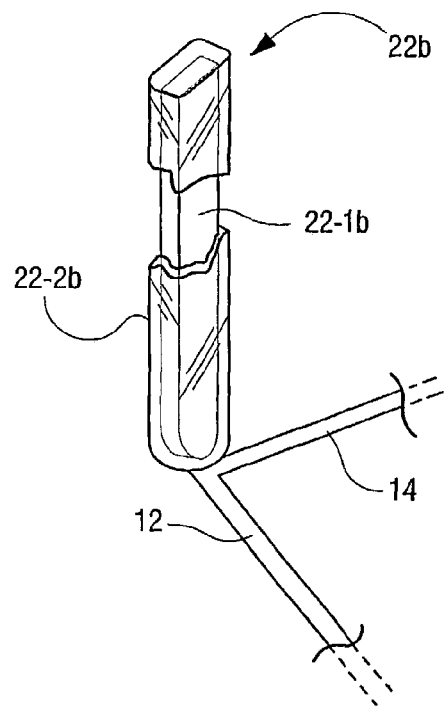

The embodiment shown in FIG. 3B is similar to that in FIG. 3A, except that the anchoring arm 22b includes an inner anchoring arm 22-1b having a substantially rectangular cross-section. The removable sleeve 22-2b thus also conformably has a substantially rectangular tubular cross-section and is formed of a molded bioabsorbable polymeric material.

Figure 3C:
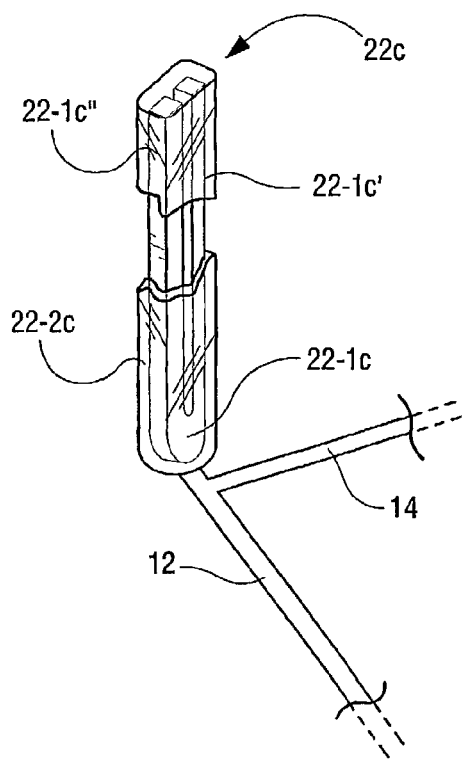

In the embodiment depicted in FIG. 3C, the inner anchoring arm 22-1c of the anchoring arm 22c is split longitudinally so as to form a pair of parallel fork arms 22-1c' and 22-1c", respectively. The molded sleeve 22-2c will thus have some of its material which occupies the spaced between the pair of fork arms 22-1c' and 22-1c" so as to provide increased traction to the sleeve, while yet still allowing for it to be removable during retrieval of the filter device 10.

Figure 3D:
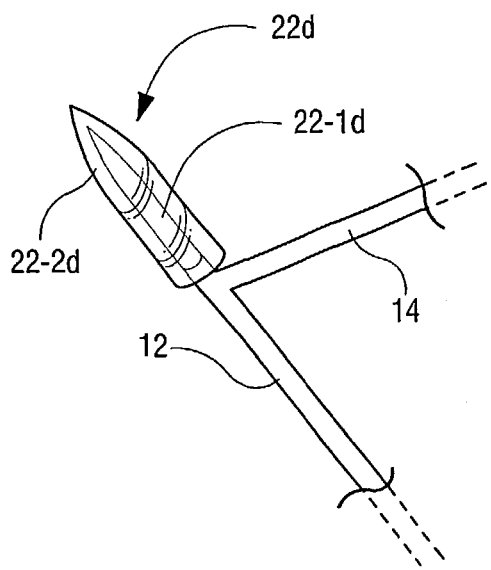
Figure 3E:
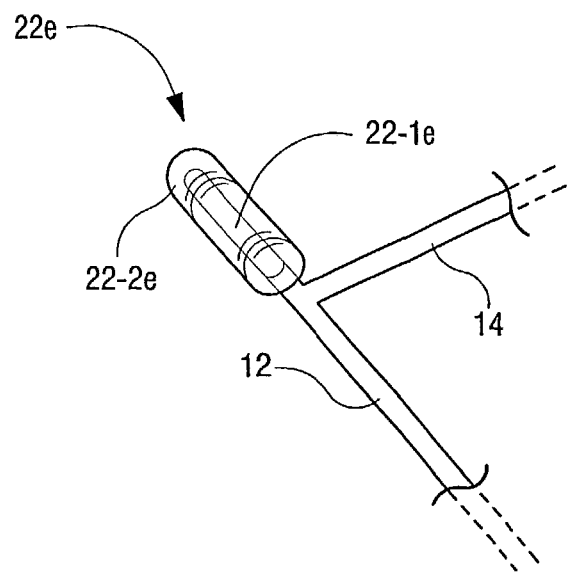
Figure 3F:
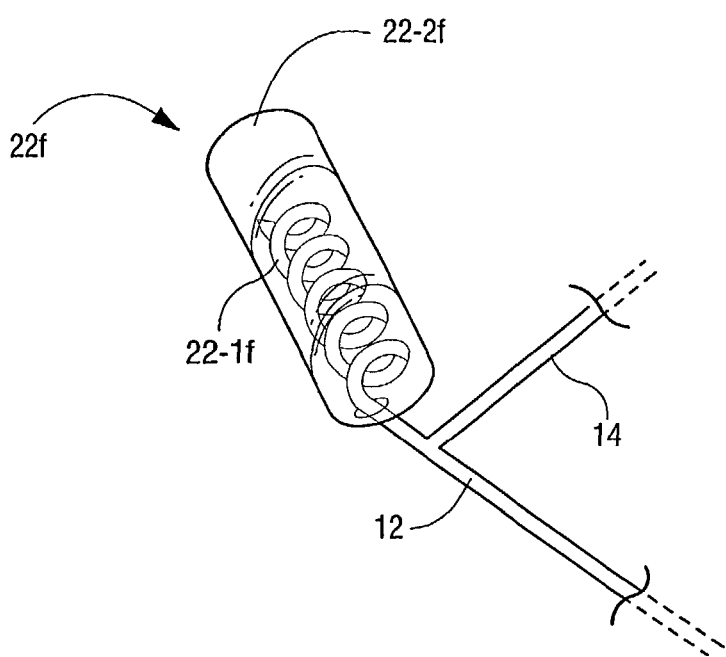

Each of the inner anchoring arms 22-1d, 22-1e and 22-1f of anchoring arms 22d, 22e and 22f shown in FIGS. 3D–3F, respectively, are relatively shorter in length as compared to the anchoring arms depicted in FIGS. 3A–3C. Furthermore, it will be noted that each of the inner anchoring arm 22-1d and its molded removable sleeve 22-2d shown in FIG. 3D has a pointed tip portion whereas the inner anchoring arm 22-1e and its molded removable sleeve 22-2e each has a rounded or blunt tip portion which may be desired in some situations as it will minimize injury to surrounding vascular tissue). The inner anchoring arm 22-1f of the anchoring arm 22f depicted in FIG. 3F has a generally helical "corkscrew" configuration. The helical inner anchoring arm 22-1f is, however, likewise covered with a molded removable sleeve 22-2f of bioabsorbable polymeric material. Thus, the helical configuration of the inner arm 22-1f provides increased drag or traction with respect to the sleeve 22-2f. On retrieval of the device 10, however, since the relative diameter of anchoring arm 22-1f is quite small, its helical configuration will yieldably straighten somewhat (i.e., in response to the force exerted on the device 10 during retrieval) to thereby allow it to be removed from its surrounding sleeve 22-2f.

Figure 4A:
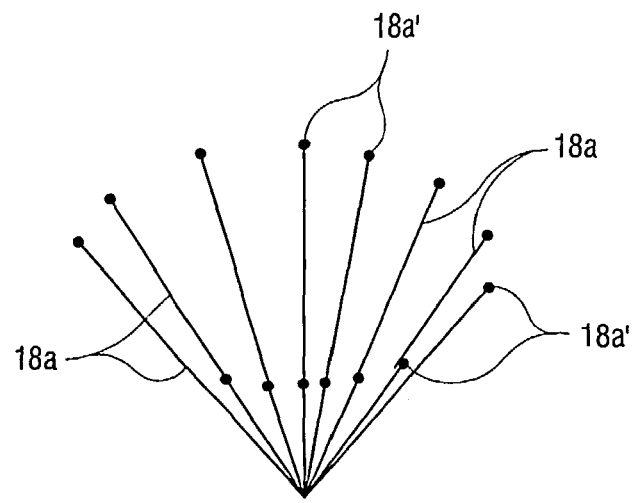
FIGS. 4A–4F are enlarged perspective views which depict a various exemplary structural embodiments of filter arms that may be employed in the vascular filters of the present invention.
Figure 4B:
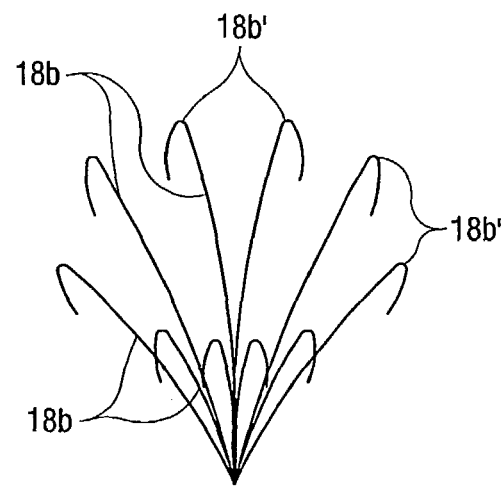
Figure 4C:
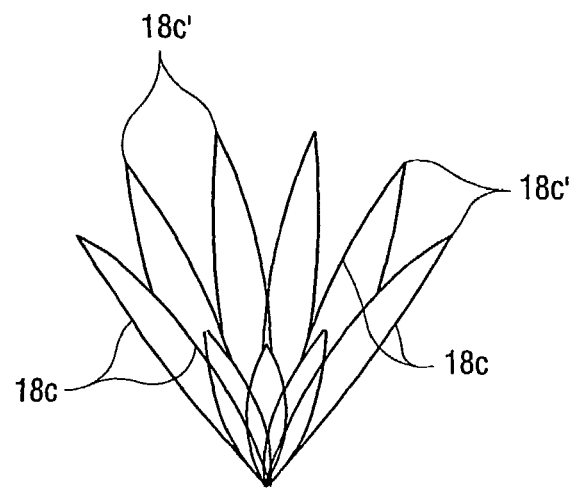
Figure 4D:
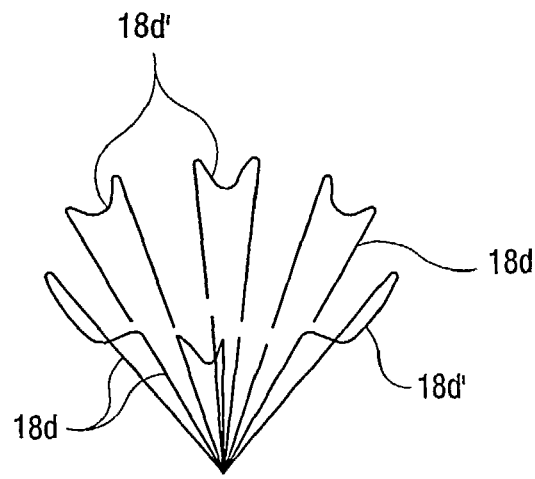
Figure 4E:
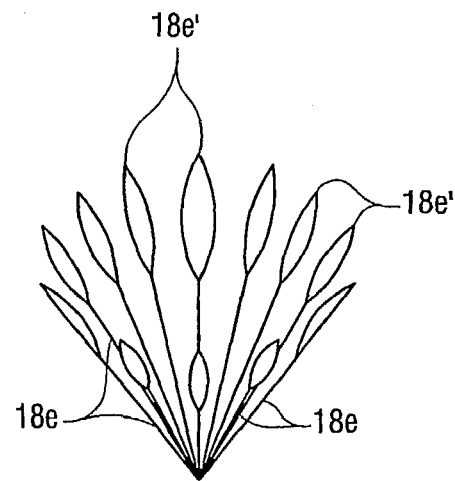
Figure 4F:
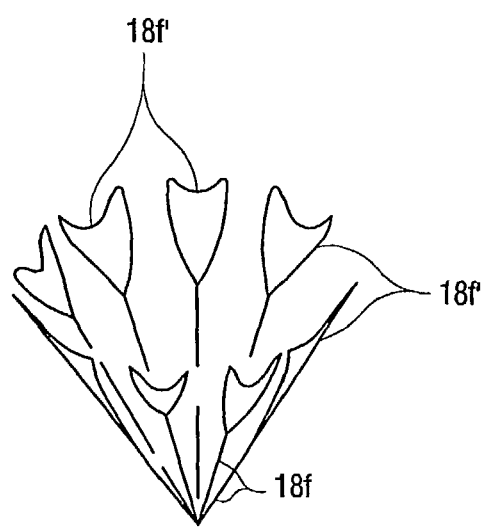

As noted previously, the distal portion of the device 10 includes a blood filter portion formed of a distally divergent plurality of filter arms. The filter arms may be provided in accordance with the present invention as a number of structural and functional variations. For example, the filter arms 18a as shown in FIG. 4A are the same as those shown in FIGS. 1A and 1B and terminate abruptly at respective terminal nodes (a few of which are identified as reference numeral 18a'). However, as shown in FIG. 4B, the terminal ends of distally divergent arms 18b may be provided as inferiorly curved sections 18b'. FIGS. 4C and 4D are similar to one another in that the respective filter arms 18c and 18d thereof are formed as elongate loops which originate and terminate at the proximal juncture thereof. The filter arms 18d of FIG. 4D, however, include a distal end portion 18d' which is curved inferiorly instead of terminating abruptly at a point as shown by the terminal ends 18c' in FIG. 4C. Similarly the filter arms 18e, 18f as shown in FIGS. 4E and 4F include distal loop portions which may terminate abruptly at ends 18e' as shown in FIG. 4E or may be interiorly curved as in ends 18f' as in FIG. 4F.

The structural components of the filter devices of this invention can be constructed from virtually any biocompatible material. Thus, for example, stainless steel, tungsten, piano wire, super elastic memory wire, chromium alloys or any other elastic memory metal wires may be used. Most preferably, the structural components of the filter devices are formed of an ally of titanium and nickel (e.g., NITINOL® alloys) due to its advantageous thermal memory and biocompatibility properties. As noted previously, however, the removable sleeves of the anchoring arms are most preferably formed of a bioabsorbable material, although they may similarly be formed of other biocompatible materials, such as NITINOL® alloys, if desired.

Figure 5A:
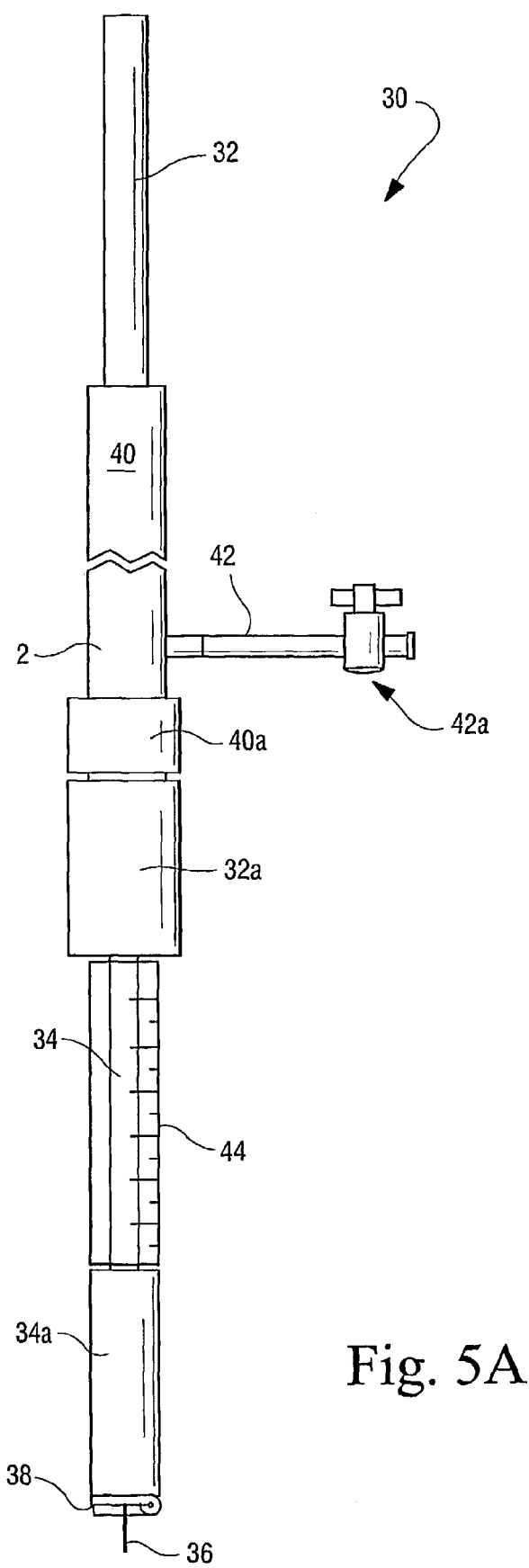
Figure 5B:
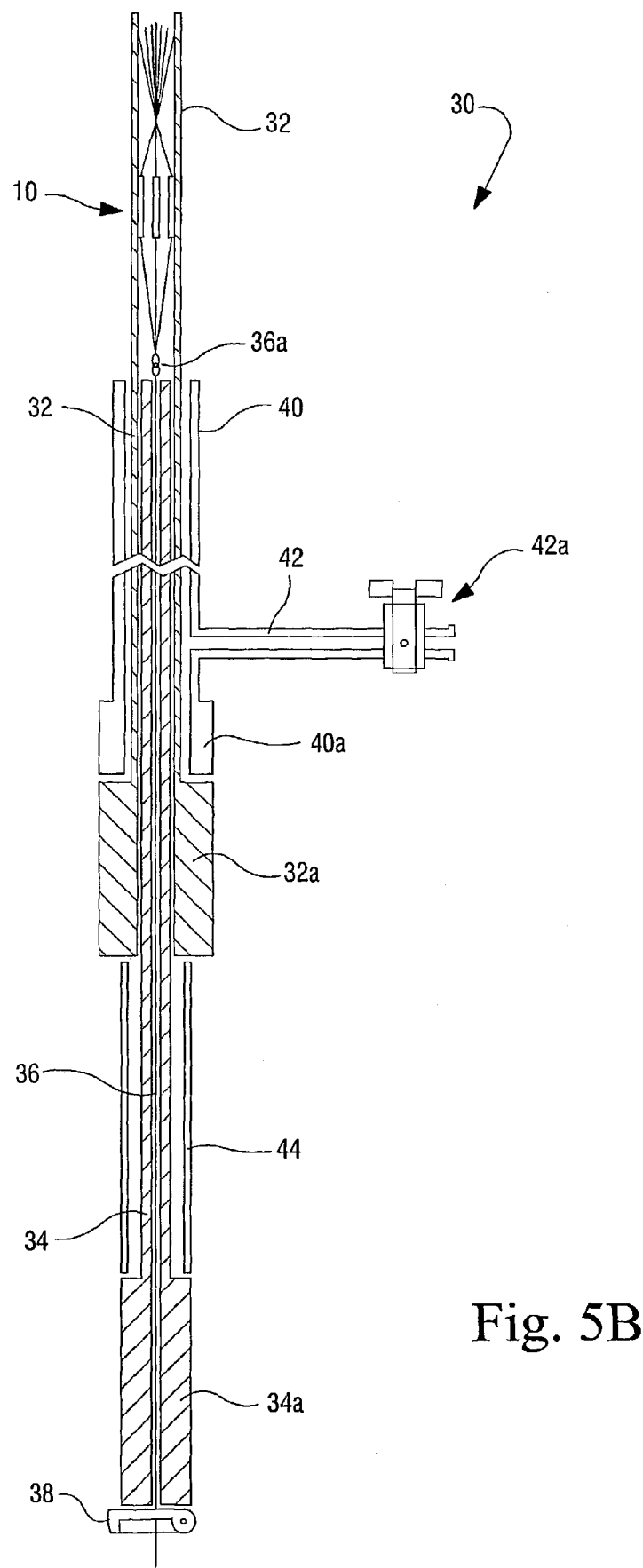
FIG. 5B is a longitudinal cross-section thereof.

Accompanying FIGS. 5A and 5B depict one particularly preferred delivery system 30 that may be employed to deliver the vascular filters 10 in accordance with the present invention. In this regard, the delivery system includes a delivery catheter 32 which is sized sufficiently so as to house therein the axially collapsed filter 10 (e.g., a size 7–8F catheter). A relatively stiff pusher catheter 34 (e.g., 5–6F catheter) is slideably received within the lumen of the delivery catheter 32 and serves to facilitate the pushing of the filter 10 beyond the distal tip of the delivery catheter 32 during deployment. An elongate conventional Gooseneck snare wire 36 extends through the pusher catheter 34 and includes a distal looped end 36a which is received within the proximal hook 16 of the filter 10. As shown in FIG. 5B, the engagement between the looped end 36a of the wire 36 and the hook 16 of the filter device 10 is secured by sliding the pusher catheter 34 over the wire 36 and locking it in place by means of a clamp 38.

The distal ends of the delivery and pusher catheters 32, 34 are provided with respective catheter hubs 32a and 34a to allow independent manipulation of each such catheter 32, 34. An outer sheath 40 is provided of sufficient size (e.g., about 9F) to allow the delivery catheter 32 to be slideably inserted within its lumen. The outer sheath 40 is considerably shorter than the delivery catheter 32 so as to allow a distal end portion of the latter to extend beyond the distalmost tip of the former. However, the outer sheath 40 is of sufficient length to permit the delivery catheter 32 to be positioned at the proper location within a patient's vascular system (e.g., beyond the confluence of the patient's iliac veins). The outer sheath 40 is provided with a proximal hub 40a. The 32a and hubs 40a may, if desired, be coupled one to another (e.g., by providing conventional Leur-type fittings) so as to enhance stability of the system 30. A side arm 42 is provided in fluid communication with the lumen of the outer sheath 40 and includes a conventional stopcock 42a to allow introduction of saline solution as may be desired by the attending physician.

The system 30 is most preferably provided initially to the attending physician in a "preloaded" state as shown in FIGS. 5A and 5B. In such a state, an adequate distance is maintained between the hub 32a of the delivery catheter 32 and the hub 34a of the pusher catheter 34 by means of a spacer tube 44. The presence of the spacer tube 44 between the hubs 32a and 34a thereby prevents accidental deployment of the filter 10 during pre-surgical handling and/or shipping of the system 30. Just prior to use, therefore, the spacer tube 34 may be removed (e.g., by cracking the tube 44 if it is formed of a sufficiently brittle material, or unwrapping it if the tube 44 is formed of a more malleable material). Removal of the spacer tube 44 thus leaves the pusher catheter 34 free to slide within the delivery catheter 32 and thus allow the attending physician to deliver the filter 10 to the appropriate location within the patient's vascular system.

FIGS. 6A–6H sequentially depict in schematic fashion deployment of a vascular filter 10 using the delivery system 30 in accordance with the present invention, whereas FIGS. 7A–D schematically show in an enlarged manner the actual deployment of the filter 10 within the patient's inferior vena cava IVC.

Figure 6A:
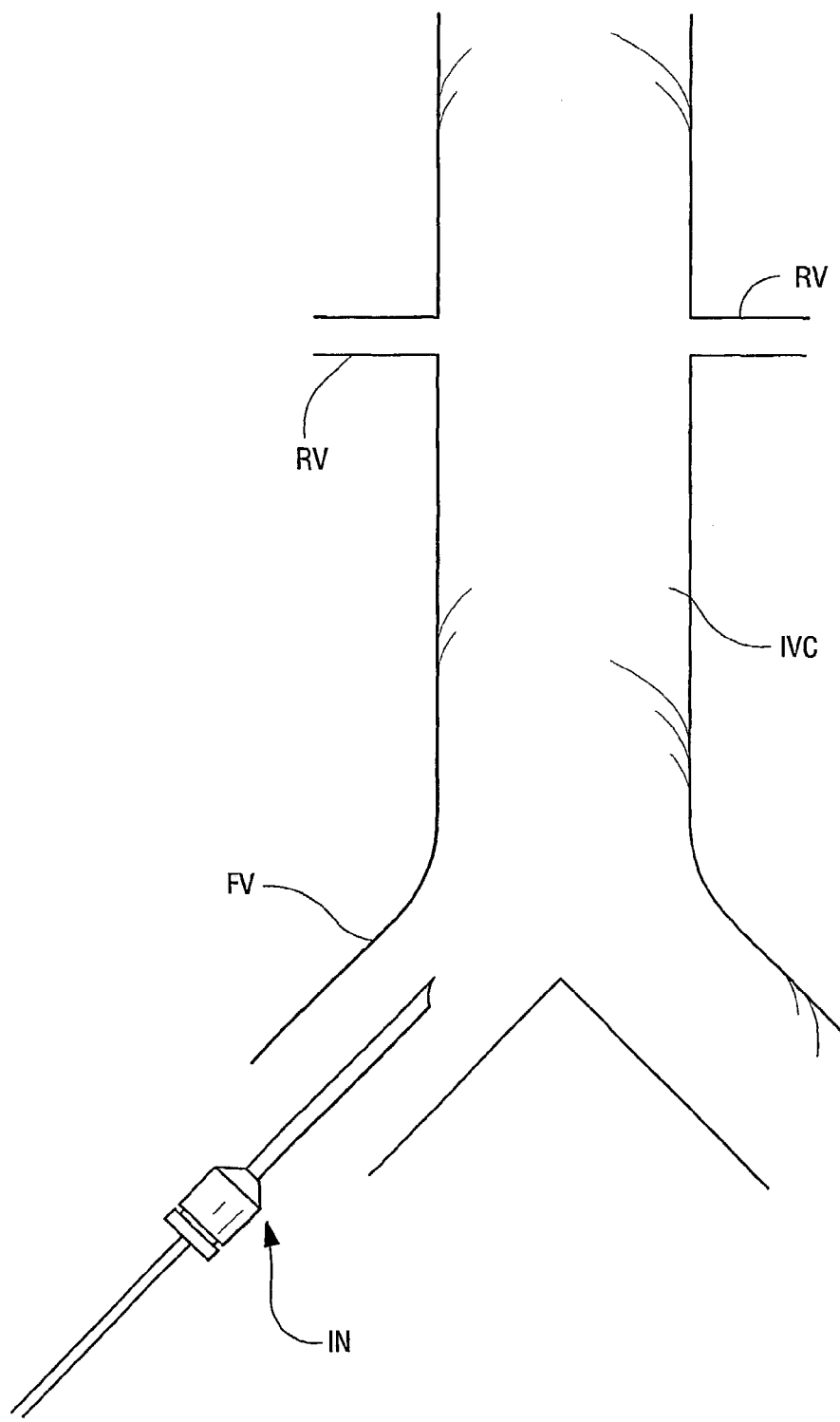
FIGS. 6A–6H depict schematically a preferred sequence to deploy the vascular filters in accordance with the present invention.
Figure 6B:
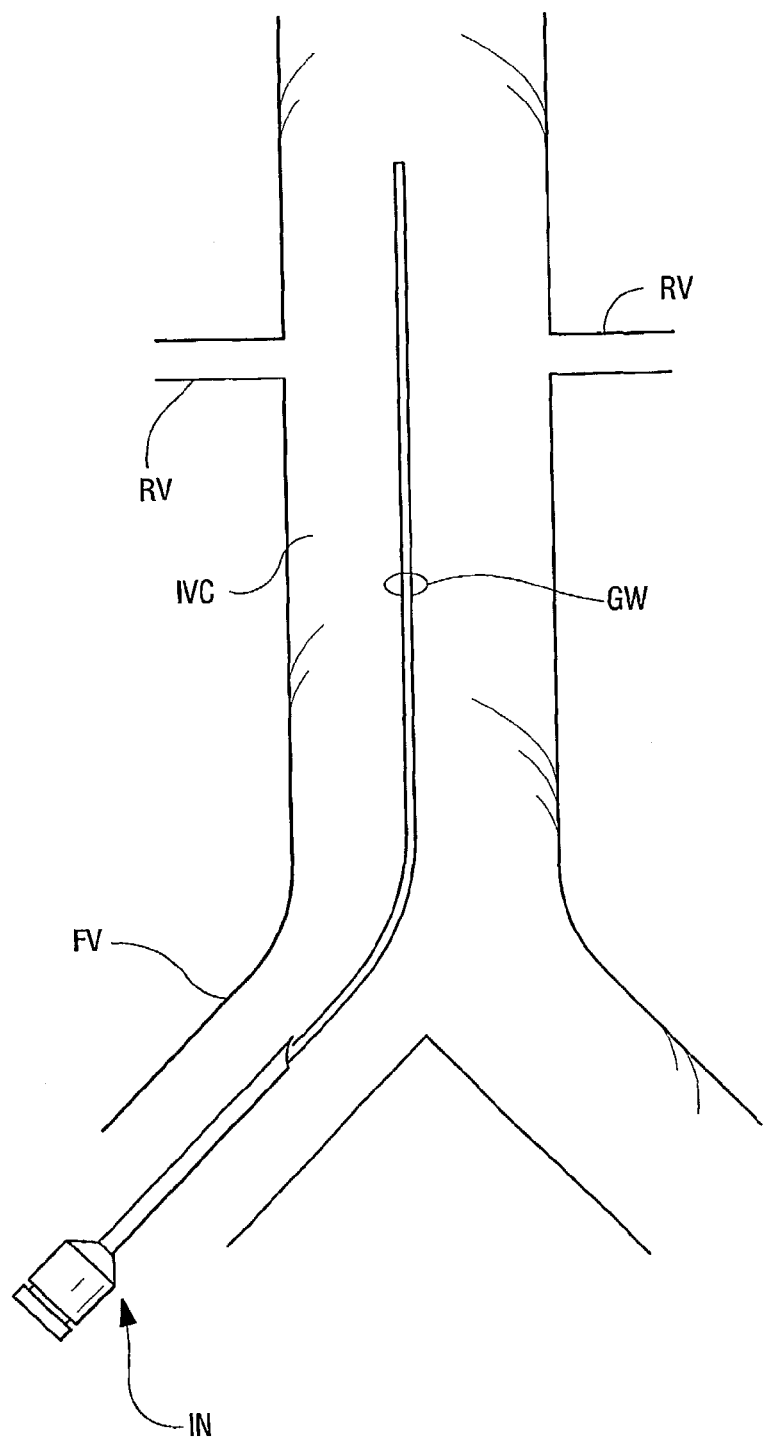
Figure 6C:
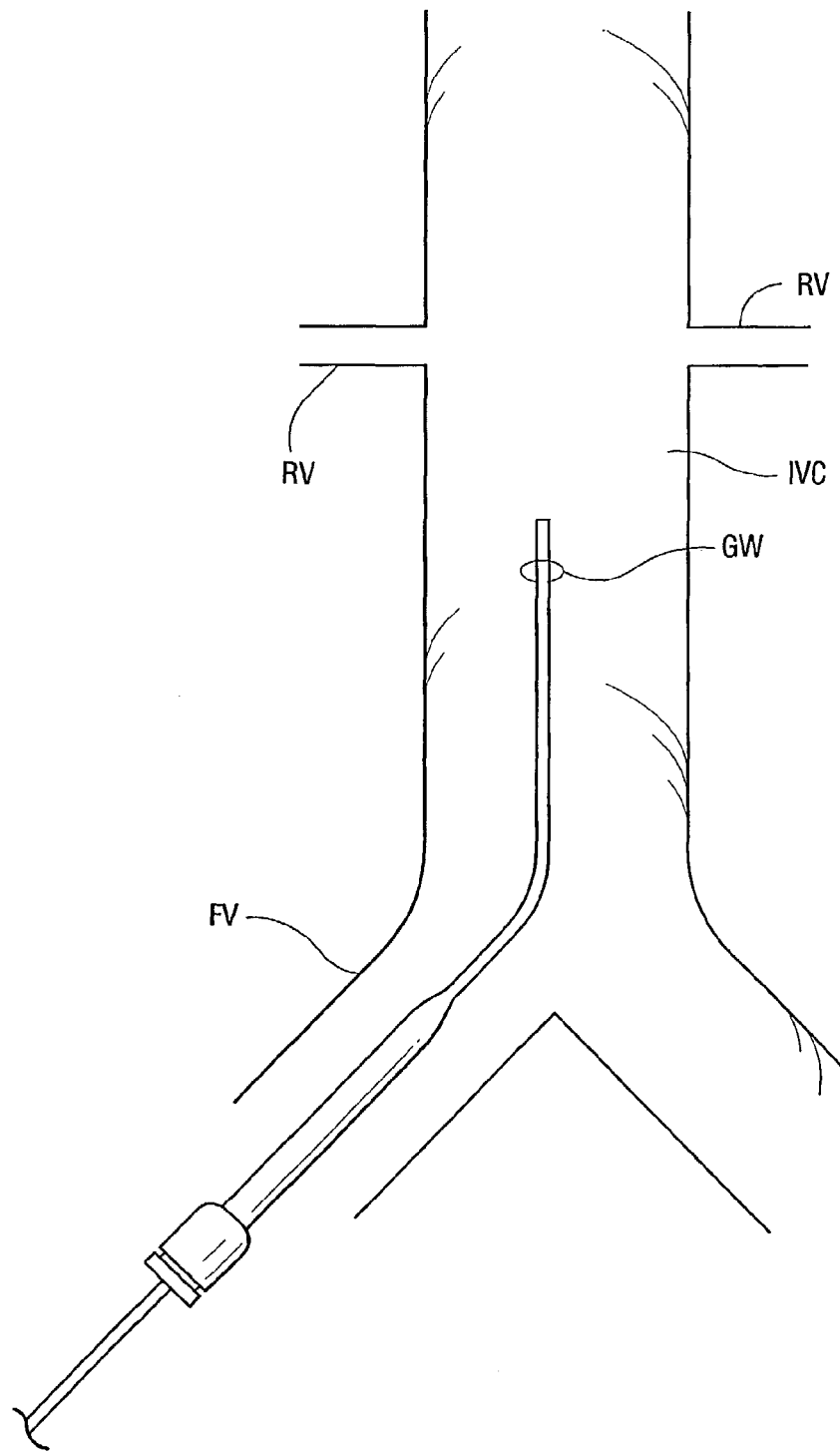
Figure 6D:
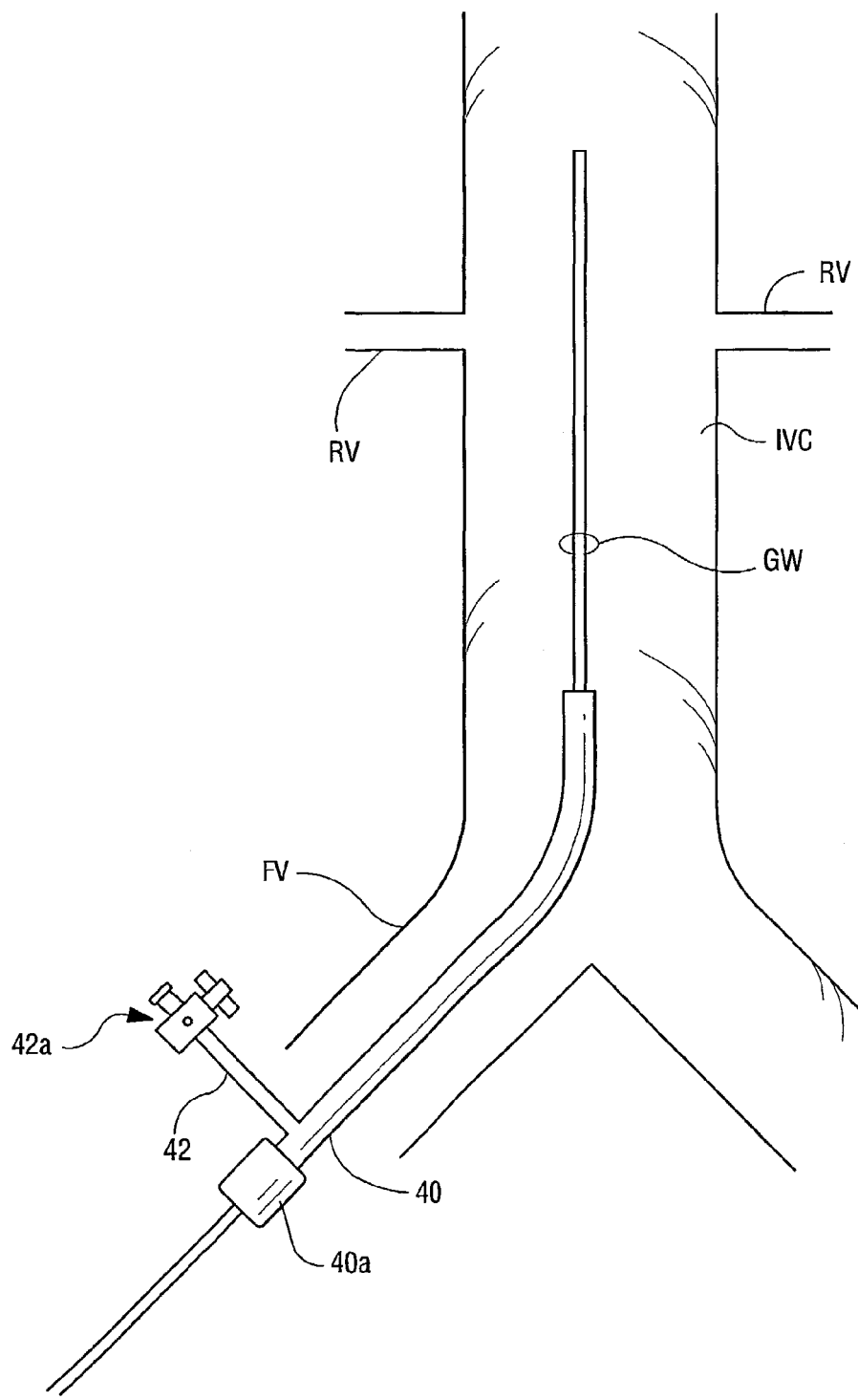
Figure 6E:
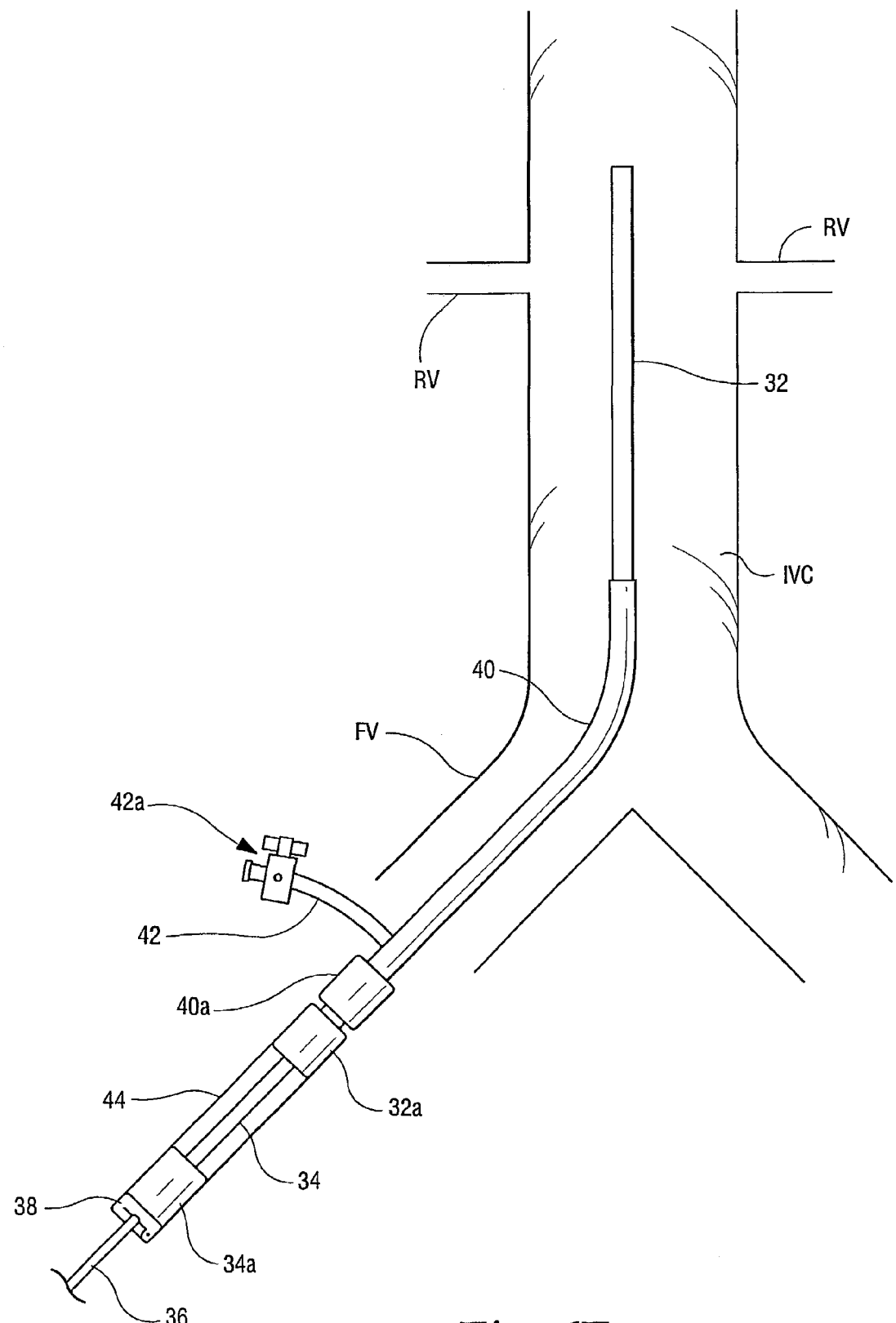
Figure 6F:
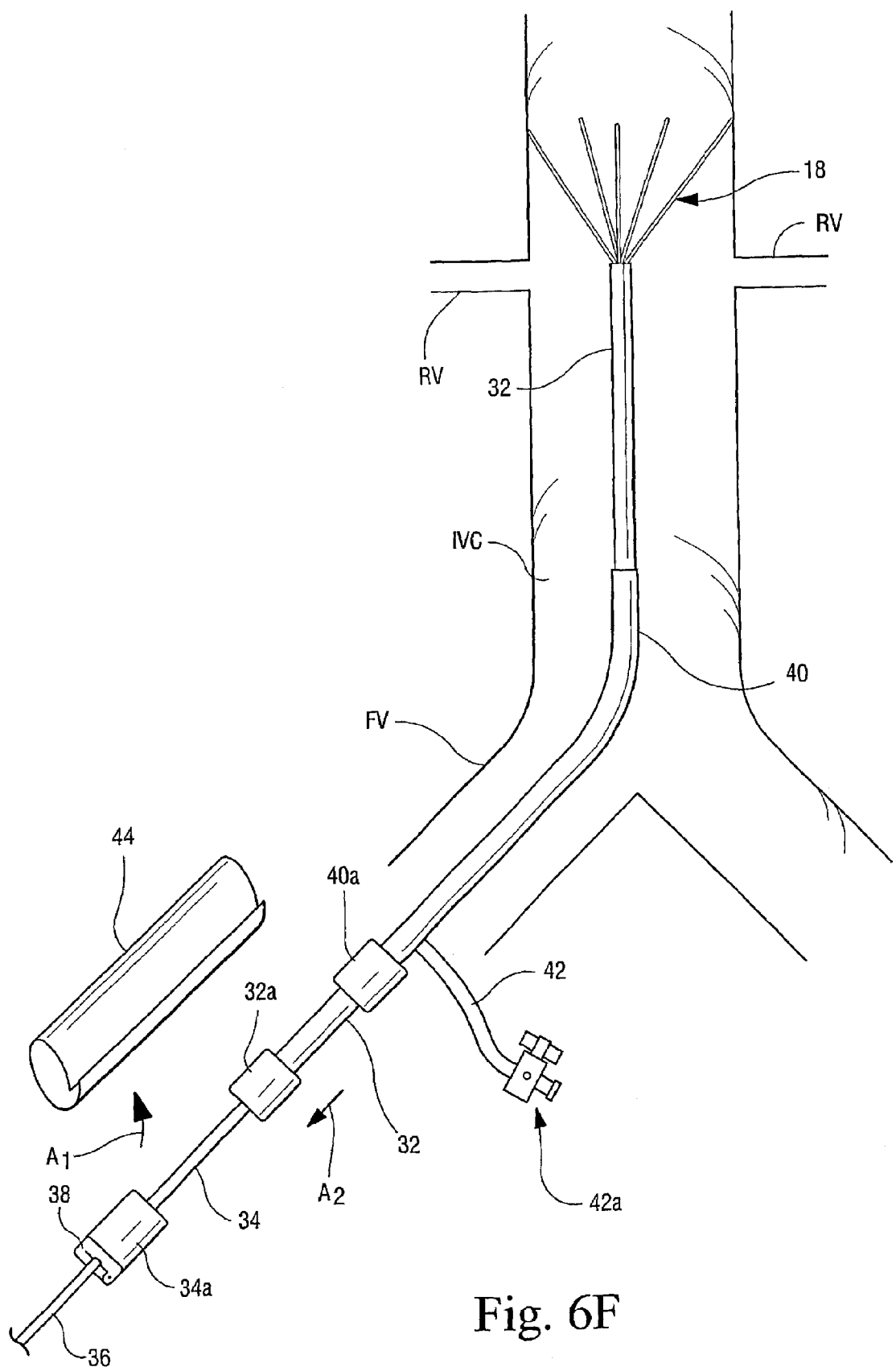
Figure 6G:
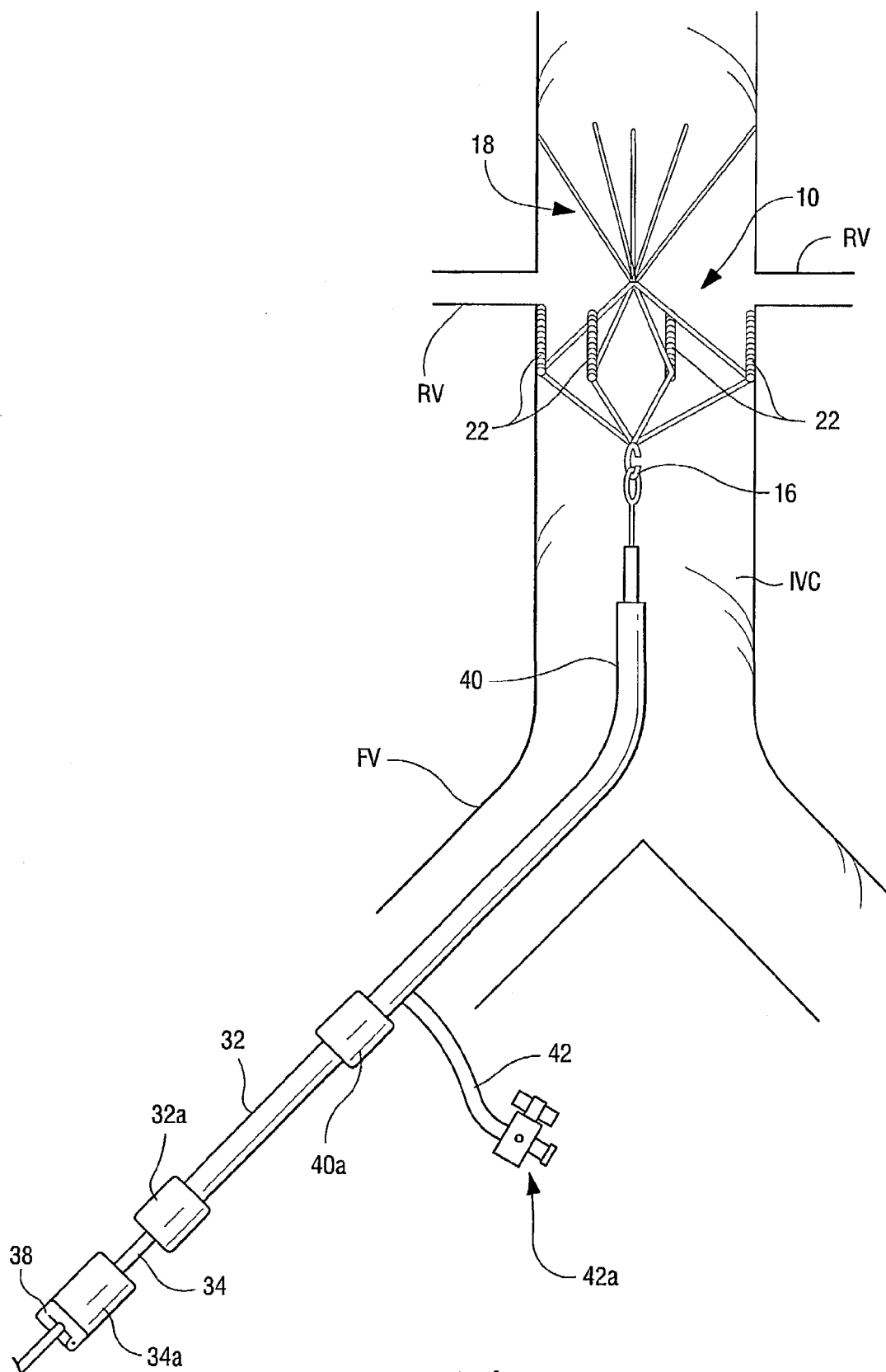
Figure 6H:
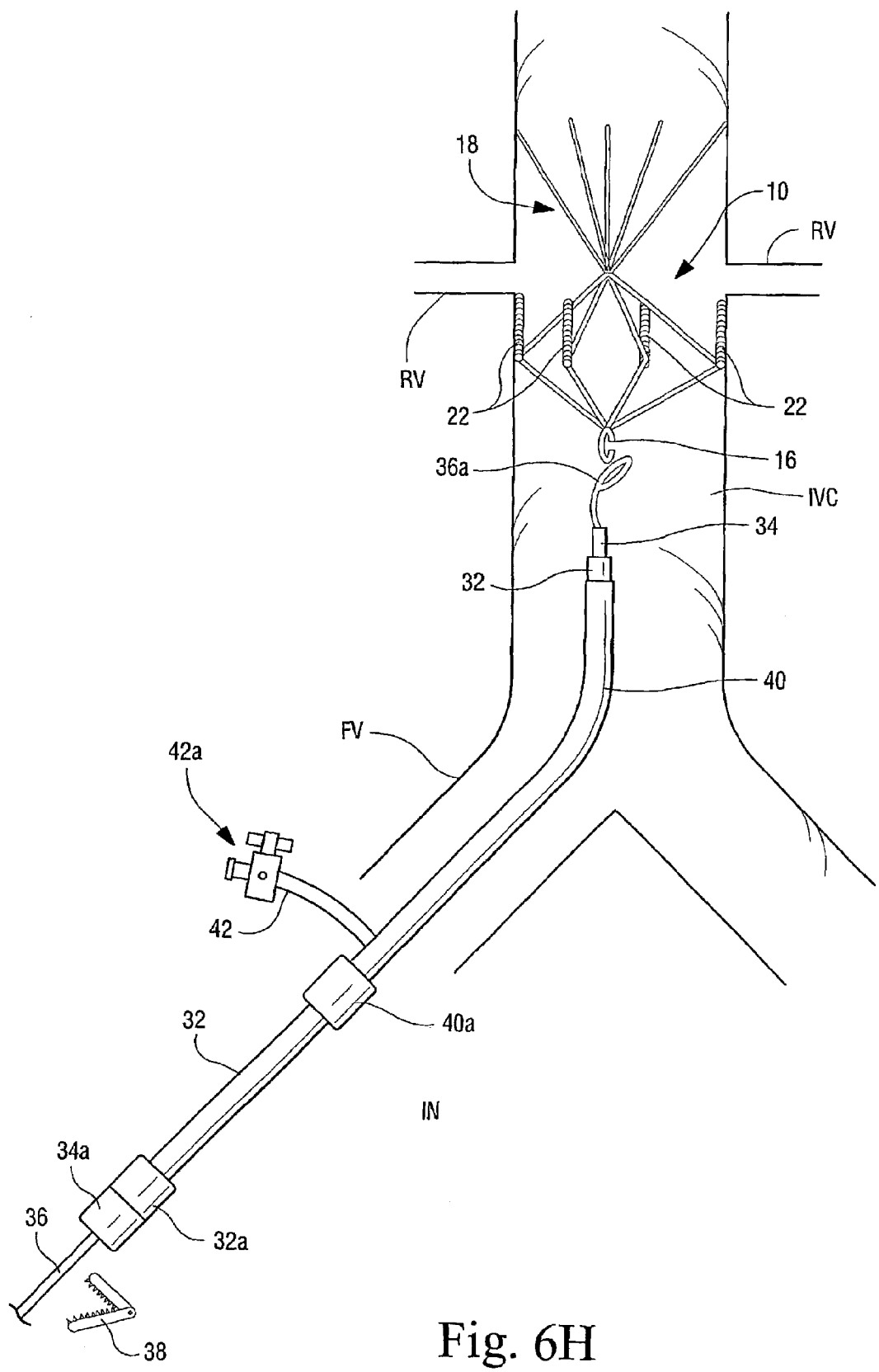
Figure 7A:
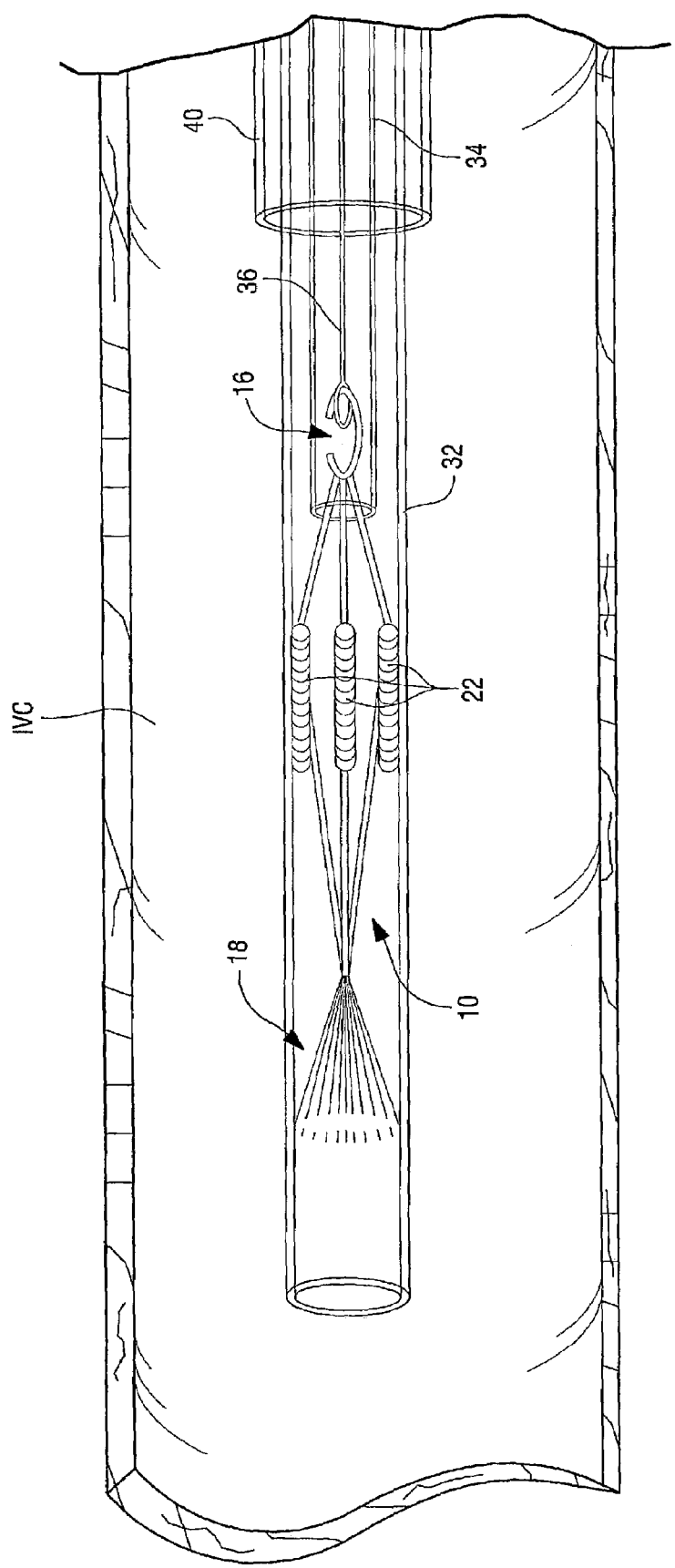
FIGS. 7A–7D depict in an enlarged schematic fashion the manner in which the vascular filters may be deployed using the deployment sequence shown in FIGS. 6A–6H.
Figure 7B:
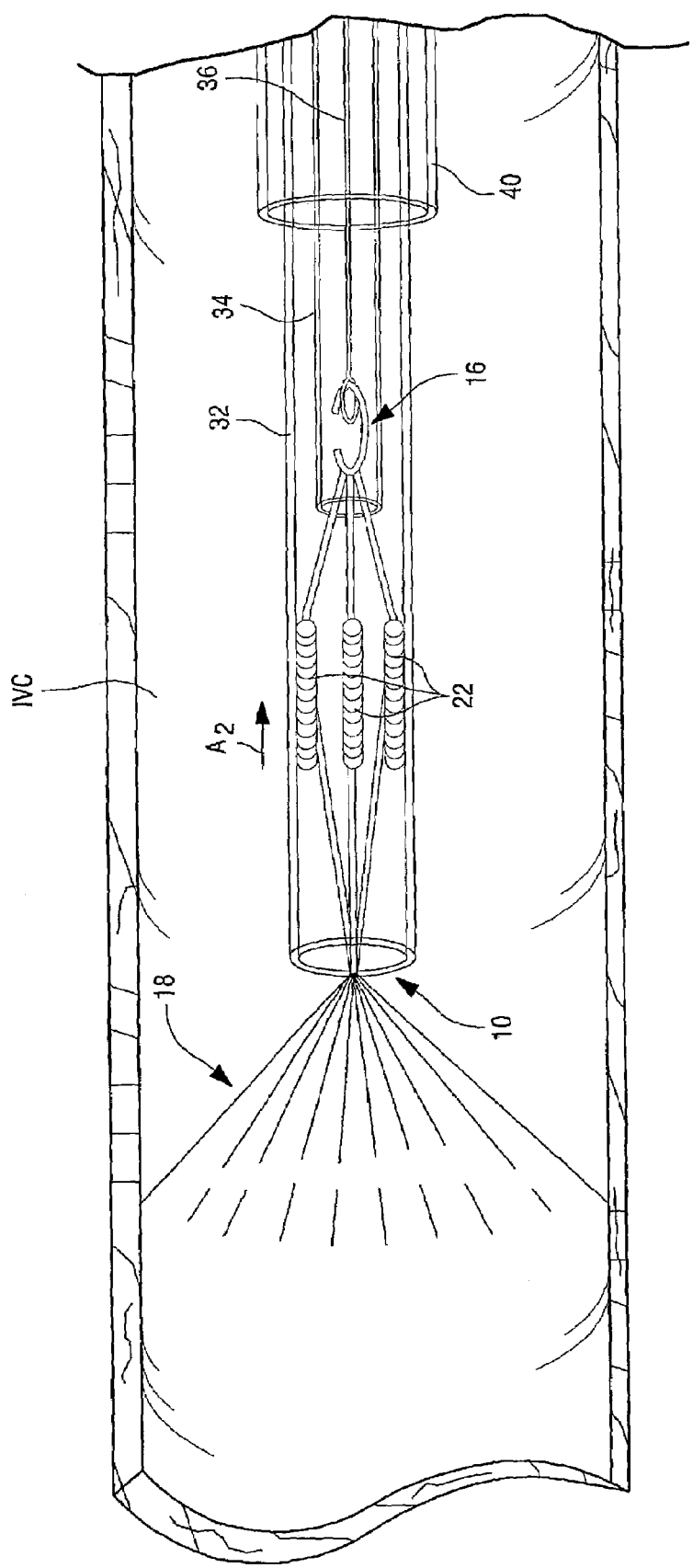
Figure 7C:
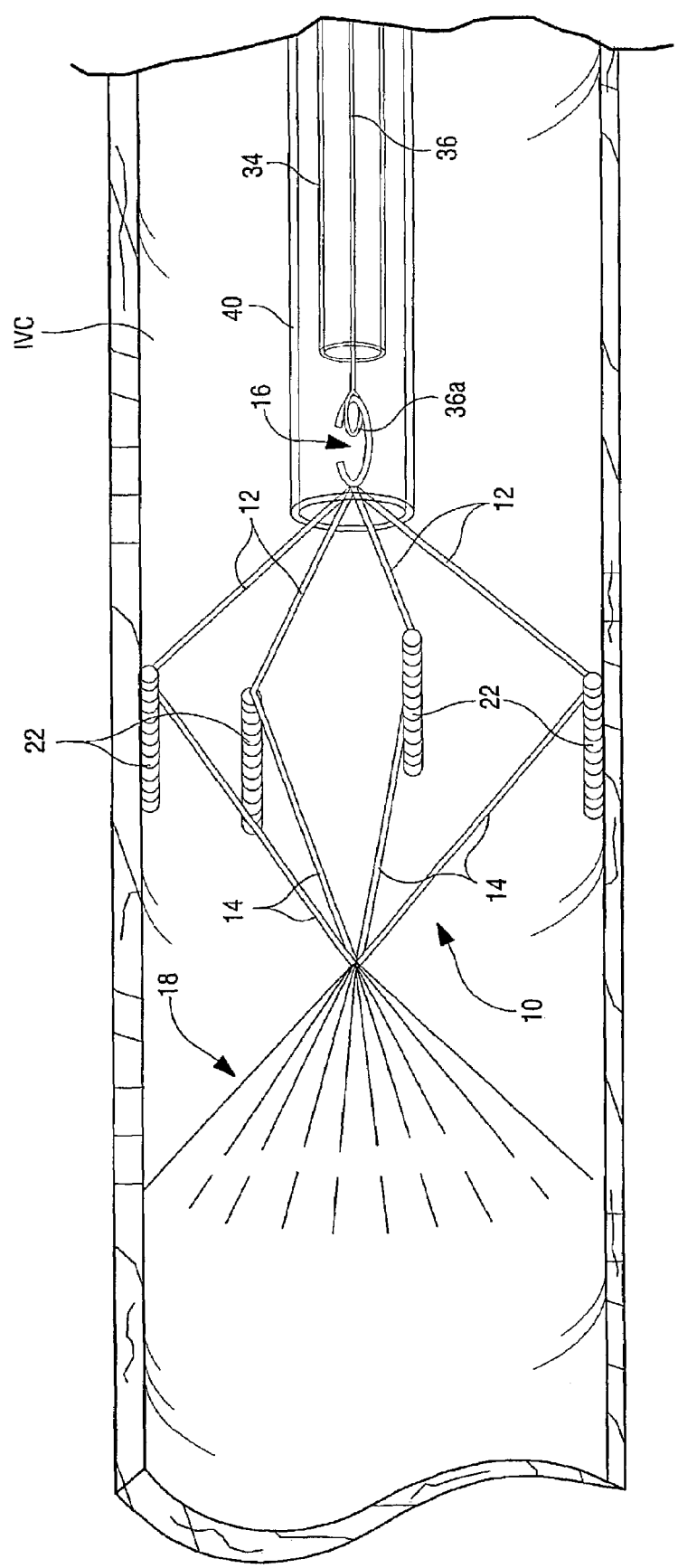
Figure 7D:
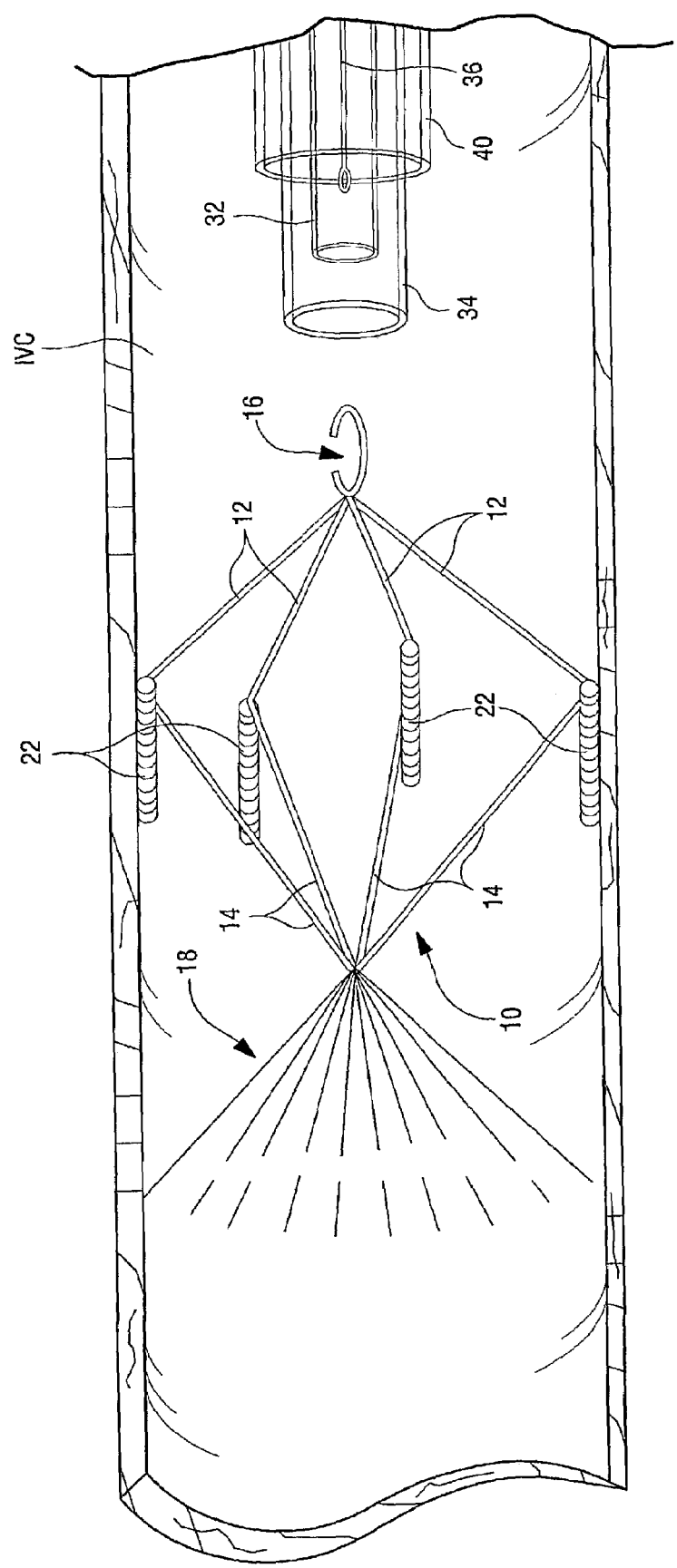

A conventional Inferior Vena Cavogram is typically performed as part of the normal advance preparation for filter placement. Thereafter, referring specifically to FIGS. 6A and 6B, the patient's femoral vein FV may be accessed using the highly conventional Seldinger technique. That is, a fine insertion needle IN is used to initially puncture the femoral vein FV as shown in FIG. 6A A guide wire GW is then threaded through the insertion needle IN within its lumen and manipulated until it is positioned in the inferior vena cava IVC (see FIG. 6B). The needle may then be removed and serial dilators (one of which is designated by the reference identifier D in FIG. 6C may be threaded over the guide wire GW. The dilator D may then be replaced with a pre-loaded filter delivery system 30 as described previously so as to allow the filter 10 in accordance with the present invention to be deployed in a sequence to be described with reference to FIGS. 6D–6H More specifically, the outer sheath 40 may initially be threaded over the guide wire GW as a replacement for the dilator D (FIG. 6D). The preloaded delivery and pusher sheaths 32, 34, respectively, separated by the spacer tube 44 may then be introduced through the lumen of the outer sheath 40 so that the distal tip of the delivery catheter 32 is positioned just above the level of the renal veins RV (see FIGS. 6E and 7A). At this time, the spacer tube 44 may be removed as shown by arrow $A_1$ in FIG. 6F. The hub 34a of the pusher catheter 34 may then be positionally restrained by the physician while the hub 32a of the delivery catheter 32 is grasped and gently pulled back in the distal direction (as shown by arrow $A_2$ in FIGS. 6F and 7B). The filter 10, and particularly the distal filter arm portion 18 thereof, will therefore responsively begin to expand as the delivery catheter 32 is withdrawn within the lumen of the outer sheath 40. The pusher catheter 34 may be used to control the final deployed position of the filter 10 by allowing the filter 10 to be pushed or pulled as desired by the physician within the inferior vena cava IVC (see FIGS. 6G and 7C). Once the filter 10 is completely deployed, the clamp 38 may be removed and the pusher catheter 34 gently withdrawn. The Gooseneck snare wire 36 is then disengaged from the proximal hook 16 of the filter 10 and the whole retrieval system 30 withdrawn from the vascular lumen (see FIGS.

6H and 7D). Gentle pressure may then be applied on the groin at the site of access, to achieve hemostasis.

Figure 8A:
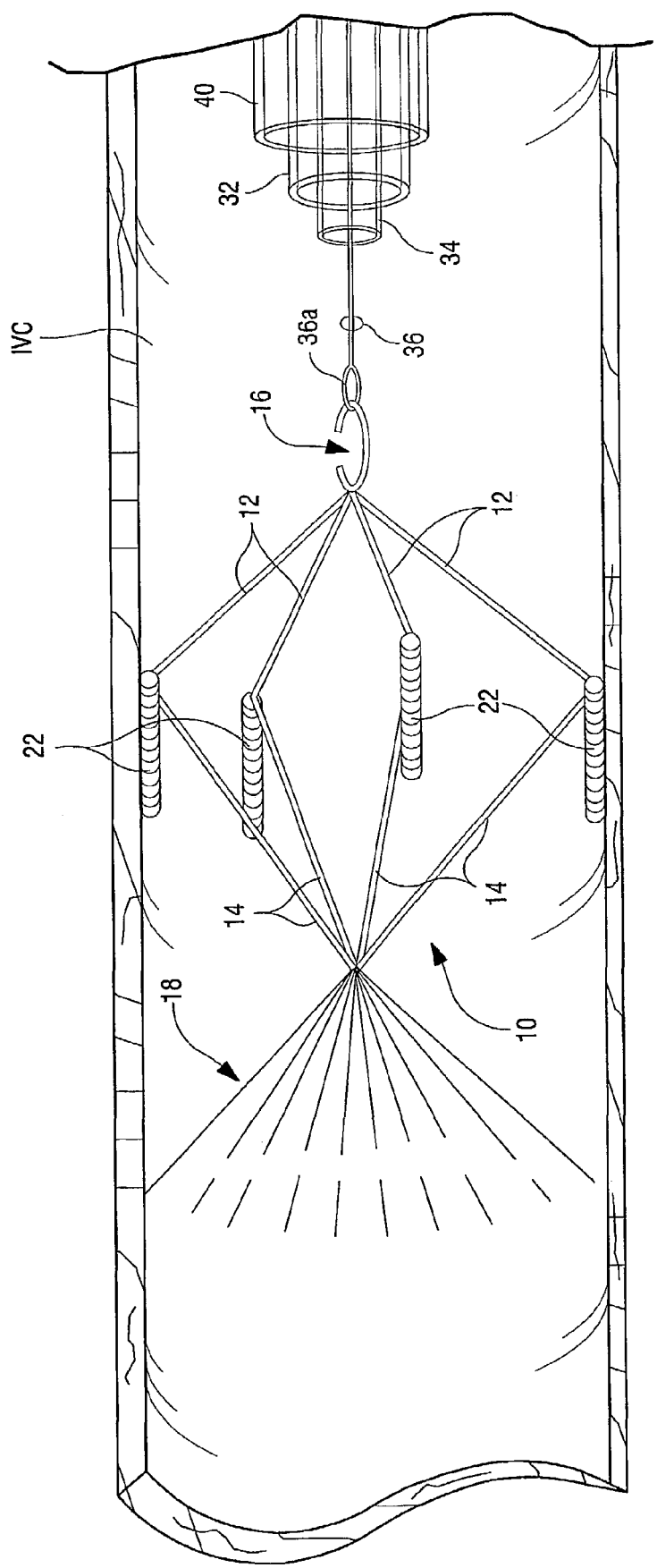
FIGS. 8A–8D depict in an enlarged schematic fashion the manner in which the vascular filters may be retrieved.
Figure 8B:
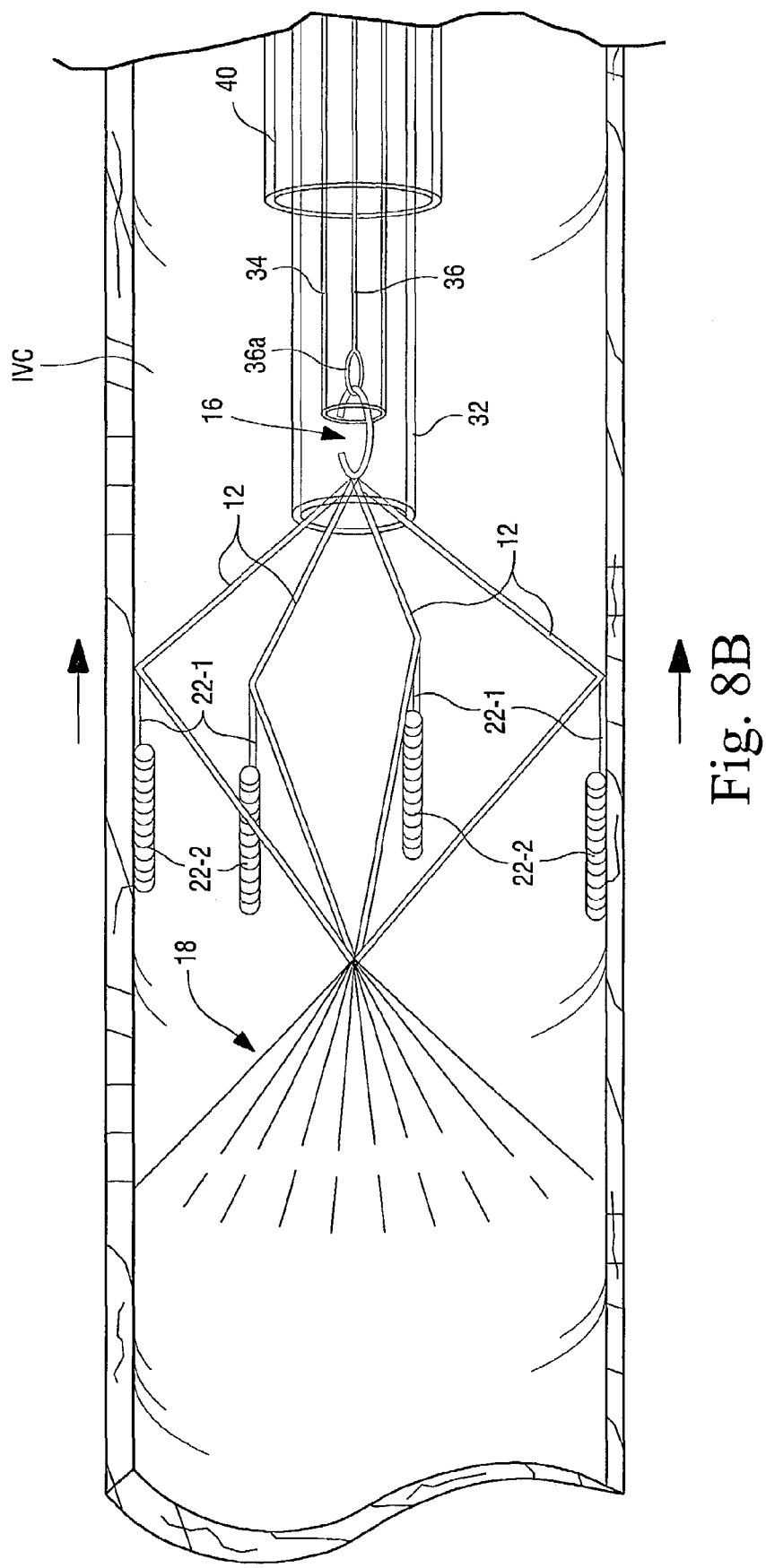
Figure 8C:
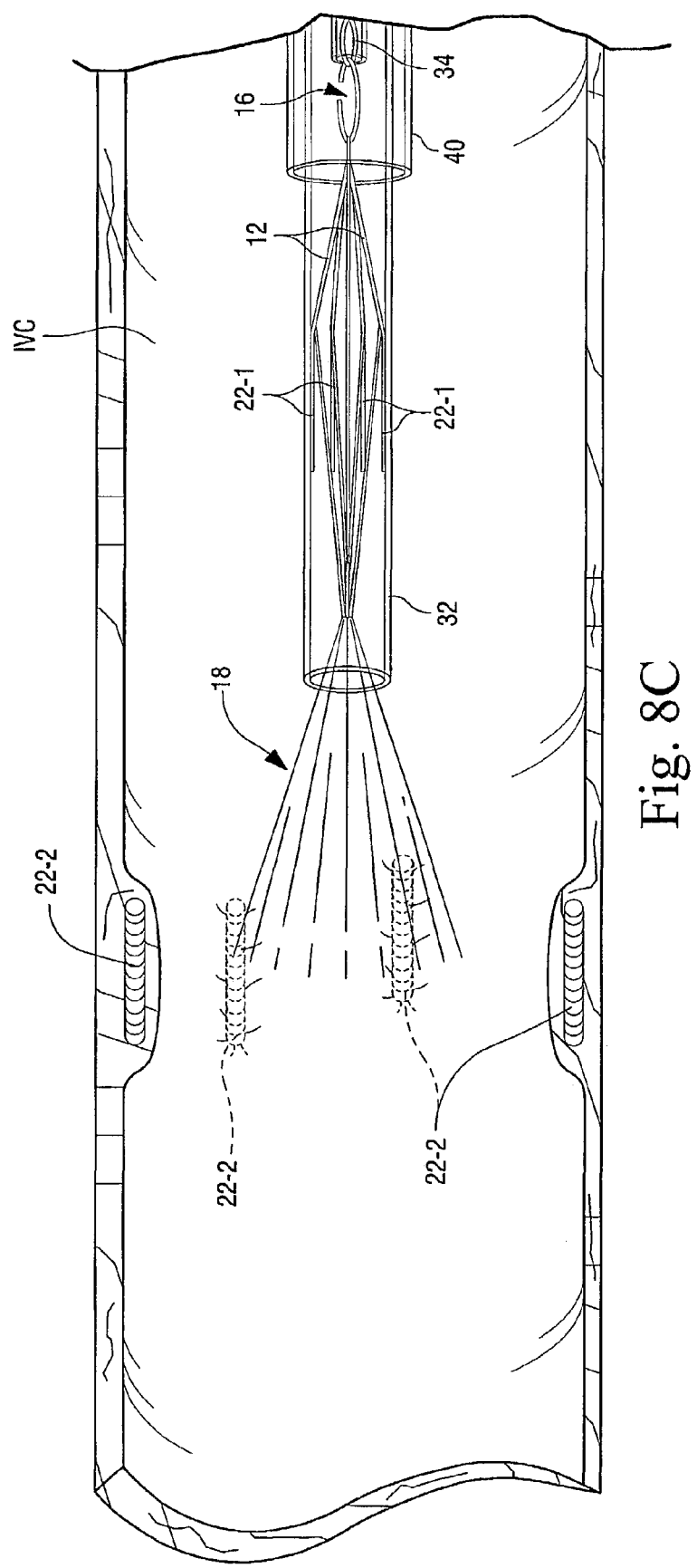
Figure 8D:
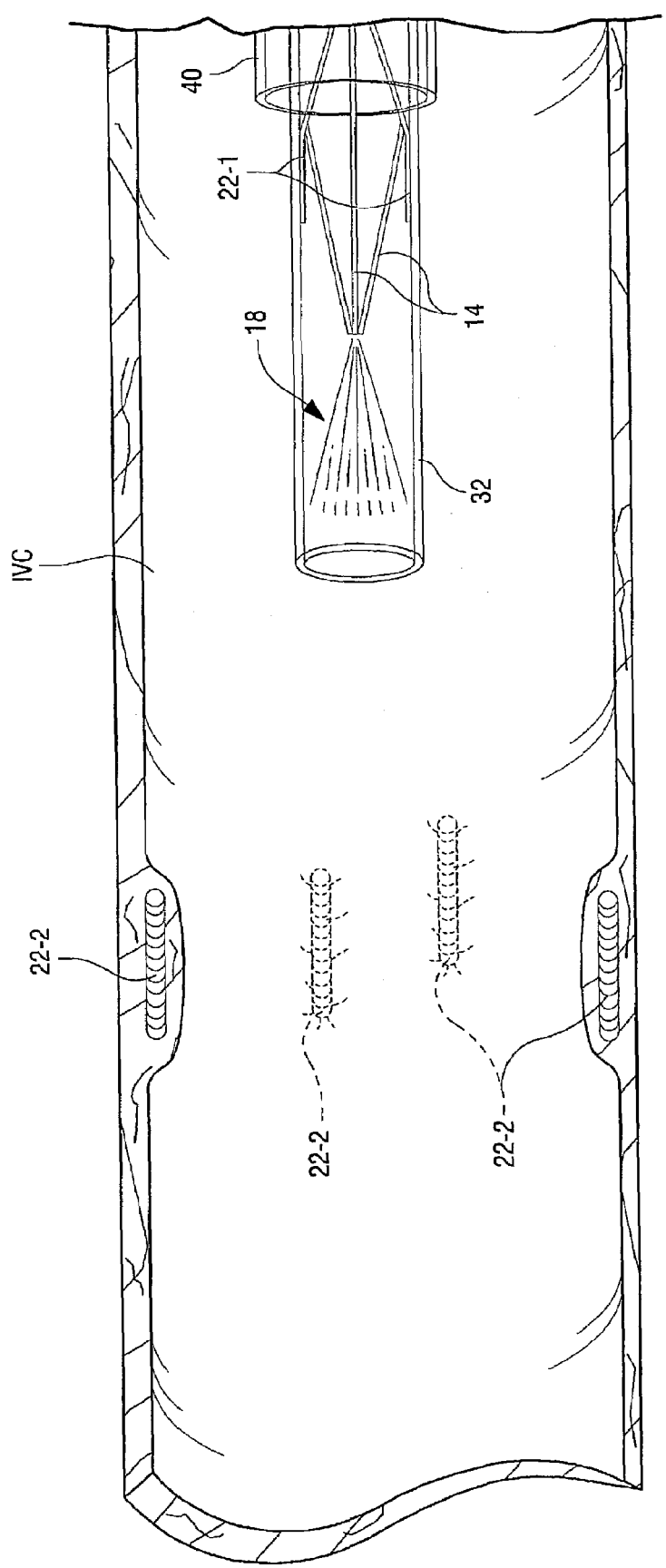

Accompanying FIGS. 8A–8D sequentially show in an enlarged manner, the sequence for retrieving the vascular filter 10 in accordance with the present invention. Similar to deployment described above with reference to FIGS. 6A–6H and 7A–7D, a retrieval catheter system essentially identical to the delivery system 30 described previously but without the pre-loaded filter therein may be positioned using the Seldinger technique. That is, after dilation, an outer sheath 40 may be introduced through which a delivery and pusher catheter 32, 34 are introduced to the site of the filter along with a Gooseneck snare wire 36. The looped end 36a of the wire 36 may then be connected to the proximal hook 16 of the filter 10 as shown in FIG. 8A. The filter 10 is then gently withdrawn into the catheter 32 which serves as a housing for the filter during retrieval. If endothelization has taken place by the time the filter 10 is retrieved, the outer sleeves 22-2 removably covering the inner anchoring arms 22-1 will be retained within the vessel wall as the proximal support arms 12 begin to be pulled gently into the distal end of catheter 32 causing the entire filter 10 to be collapsed onto its elongate axis $A_l$ (FIG. 8B). The filter 10 in the catheter 32 can then be withdrawn into the outer sheath 40 and the whole system may then withdrawn from the vessel lumen (FIG. 8D) leaving the endothelized outer sleeves 22-2 behind. As described previously, the outer sleeves 22-2 will be hydrolyzed and absorbed over time since it is made of a bioabsorbable polymeric material.

Figure 9A:
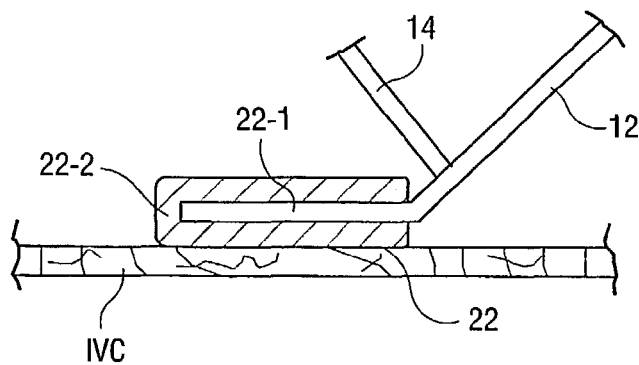
FIGS. 9A–9D are greatly enlarged schematic cross-sectional views showing a representative anchor arm during the filter retrieval sequence.
Figure 9B:
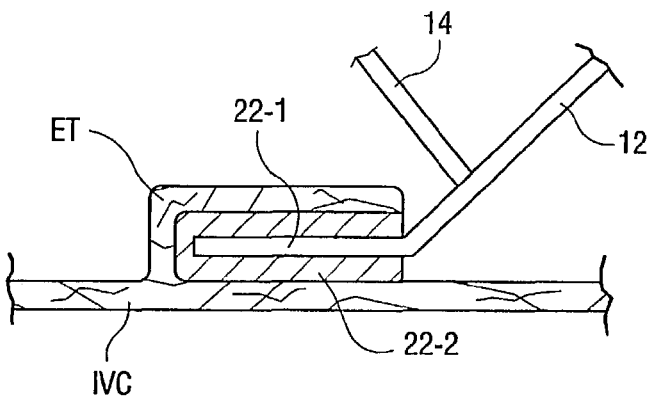
Figure 9C:
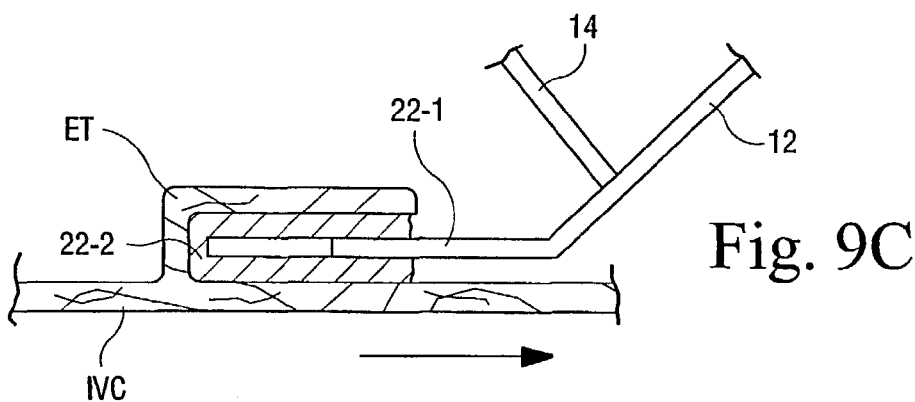
Figure 9D:
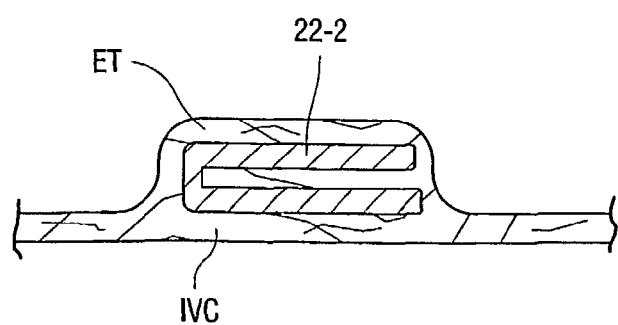

FIGS. 9A–9D 9D are greatly enlarged schematic cross-sectional views showing a representative anchor arm 22 during the filter retrieval sequence. As shown in FIG. 9A, the exemplary anchoring arm 22 comprised of an inner arm 22-1 and a removable outer sleeve 222 formed of a bioabsorbable polymeric material may be positioned within a patient's inferior vena cava IVC as has been previously described. Over time, endothelization of the anchoring arm will typically occur as shown in FIG. 9B by the endothelial tissue ET. Upon retrieval, the outer sleeve 22-2 will therefore remain positionally fixed to the vessel wall by virtue of such endothelization while the inner anchoring arm 22-1 is withdrawn therefrom in the direction of arrow $A_3$ in FIG. 9C. The outer sleeve 22-2 will thus remain behind in the vessel wall as shown in FIG. 9D following removal of the other structural components associated with the filter 10. However, since the sleeve 22-2 is formed of a bioabsorbable polymeric material, it will eventually disappear over time. In such a manner, the filters 10 of the present invention allow relatively easy retrieval while minimizing (if not preventing entirely) harm to the vascular endothelium.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A blood filter sized and configured to be positioned within a vascular vessel, the blood filter comprising:
    a distal filter portion which includes a plurality of distally divergent filter arms;
    a support portion proximally disposed and connected to said filter portion, wherein said support portion includes a plurality of distal and proximal support arms connected at respective intermediate junctures; and
    a plurality of anchoring arms extending from respective ones of said intermediate junctures for temporarily anchoring the blood filter to a wall of the vascular vessel, wherein
    said anchoring arms include an inner anchoring arm and an outer sleeve removably covering a portion of said inner anchoring arm.

2. The filter of claim 1, wherein said outer sleeve comprises a bioabsorbable polymeric material.

3. The filter of claim 2, wherein said sleeve comprises a length of monofilament formed of said bioabsorbable polymeric material wound around said portion of said inner anchoring arm.

4. The filter of claim 2, wherein said outer sleeve comprises a generally tubular element molded from said bioabsorbable polymeric material.

5. A vascular filter for implanting within a blood vessel comprising:
    a distal filter portion which includes a plurality of distally divergent filter arms;
    a proximal support portion connected to said filter portion and having a plurality of circumferentially spaced-apart anchoring arms which include an inner anchoring arm and a removable sleeve covering said inner anchoring arm, wherein the sleeve comprises a length of monofilament which is wrapped around said inner anchoring arm, the monofilament being formed of a bioabsorbable polymeric material,
    wherein said sleeve is detachable from said inner anchoring arm during removal of said proximal support portion from the blood vessel.

6. The filter of claim 2 or 5, wherein said bioabsorbable polymeric material is a hydrolyzable polymer.

7. The filter of claim 1 or 5, wherein said inner anchoring arm has a generally round or rectangular cross-section.

8. The filter of claim 1 or 5, wherein said inner anchoring arm has a longitudinal split.

9. The filter of claim 1 or 5, wherein said inner anchoring arm has a generally helical configuration.

10. The filter of claim 1 or 5, wherein at least some of said filter arms are inferiorly curved.

11. The filter of claim 1 or 5, wherein at least some of said filter arms are formed of elongate loops.

12. The filter of claim 1 or 5, wherein at least some of said filter arms include a distal loop.

13. The filter of claim 5, wherein
    said support portion includes a plurality of distal and proximal support arms connected at respective intermediate junctures; and wherein
    said inner anchoring arms extend from respective ones of said intermediate junctures of said distal and proximal support arms.

14. The filter of claim 13, further comprising a plurality of extension arms which join respective ones of said inner anchoring arms and said intermediate junctures.

15. A blood vessel filter, comprising:
    a collapsible body, said collapsible body being collapsible toward a longitudinal axis for insertion into a blood vessel and being expandable for anchoring said blood vessel filter to a wall of said blood vessel, said collapsible body having proximal and distal ends;
    a filter portion attached to said collapsible body at said distal end;
    a plurality of spaced inner anchoring arms extending from said collapsible body, said anchoring arms contacting said wall of said blood vessel when said collapsible body is expanded; and a plurality of removable sleeves fitted over said anchoring arms; wherein said sleeves are detachable from said anchoring arms during removal of said collapsible body from said blood vessel, wherein said filter portion includes a plurality of distally divergent filter arms; and wherein said filter comprises a support portion proximally disposed and connected to said filter portion, wherein said support portion includes a plurality of distal and proximal support arms connected at respective intermediate junctures; wherein said inner anchoring arms extend from respective ones of said intermediate junctures of said distal and proximal support arms.

16. The filter of claim 15, further comprising a plurality of extension arms which join respective ones of said inner anchoring arms and said intermediate junctures.

17. The filter of claim 15 or 16, wherein said sleeve comprises a length of monofilament formed of said bioabsorbable polymeric material wound around said portion of said inner anchoring arm.

18. The filter of claim 15 or 16, wherein said outer sleeve comprises a generally tubular element molded from said bioabsorbable polymeric material.

19. The filter of claim 15 or 16, wherein said sleeve is formed of a hydrolyzable polymeric material.

* * * * *